United States Patent
Park et al.

(10) Patent No.: US 10,667,714 B2
(45) Date of Patent: Jun. 2, 2020

(54) METHOD AND SYSTEM FOR DETECTING INFORMATION OF BRAIN-HEART CONNECTIVITY BY USING PUPILLARY VARIATION

(71) Applicants: SANGMYUNG UNIVERSITY INDUSTRY-ACADEMY COOPERATION FOUNDATION, Jongno-gu, Seoul (KR); CENTER OF HUMAN-CENTERED INTERACTION FOR COEXISTENCE, Seongbuk-gu, Seoul (KR)

(72) Inventors: Sang In Park, Seoul (KR); Sungchul Mun, Seoul (KR); Dong Won Lee, Seongnam-si (KR); Myoung Ju Won, Cheonan-si (KR); Min Cheol Whang, Goyang-si (KR)

(73) Assignees: SANGMYUNG UNIVERSITY INDUSTRY-ACADEMY COOPERATION FOUNDATION, Seoul (KR); CENTER OF HUMAN-CENTERED INTERACTION FOR COEXISTENCE, Seoul (KR)

( * ) Notice: Subject to any disclaimer, the term of this patent is extended or adjusted under 35 U.S.C. 154(b) by 233 days.

(21) Appl. No.: 15/869,722

(22) Filed: Jan. 12, 2018

(65) Prior Publication Data
US 2018/0235498 A1  Aug. 23, 2018

(30) Foreign Application Priority Data
Feb. 17, 2017 (KR) .......................... 10-2017-0021520
Nov. 7, 2017 (KR) .......................... 10-2017-0147608

(51) Int. Cl.
*A61B 5/0456* (2006.01)
*A61B 3/11* (2006.01)
(Continued)

(52) U.S. Cl.
CPC ........ *A61B 5/0456* (2013.01); *A61B 5/04012* (2013.01); *A61B 5/04845* (2013.01);
(Continued)

(58) Field of Classification Search
CPC . A61B 5/0402; A61B 5/04012; A61B 5/0456; A61B 5/0205; A61B 3/112
See application file for complete search history.

(56) References Cited

U.S. PATENT DOCUMENTS 10,290,139 B2 * 5/2019 Won .................. G06T 13/40

FOREIGN PATENT DOCUMENTS

| CN | 104586386 A | 5/2015 |
| CN | 105030258 A | 11/2015 |

(Continued)

OTHER PUBLICATIONS

Ohl, S., Microsaccades are coupled to heartbeat, 2016, Journal of Neuroscience, 36(4), 1237-1241 (Year: 2016).*
(Continued)

*Primary Examiner* — David J. McCrosky
*Assistant Examiner* — Chanel J Jhin
(74) *Attorney, Agent, or Firm* — Buchanan Ingersoll & Rooney PC

(57) ABSTRACT

Provided are a method and system for detecting information of brain-heart connectivity, the method comprising: obtaining moving images of a pupil and an electrocardiogram (ECG) signal from a subject; acquiring a pupil size variation (PSV) from the moving images by separating the moving images at a predetermined time range after R-peak of the ECG signal; extracting signals of a first period and a second
(Continued)

period from the PSV; calculating alpha powers of the signals of the first and second periods at predetermined frequencies respectively.

6 Claims, 17 Drawing Sheets

(51) Int. Cl.
    *A61B 5/0484*     (2006.01)
    *A61B 5/04*     (2006.01)
    *A61B 5/16*     (2006.01)
    A61B 5/0478     (2006.01)
    A61B 5/00     (2006.01)
    A61B 5/048     (2006.01)

(52) U.S. Cl.
    CPC ............... *A61B 5/163* (2017.08); *A61B 5/048* (2013.01); *A61B 5/0478* (2013.01); *A61B 5/4064* (2013.01); *A61B 5/7264* (2013.01)

(56) References Cited

FOREIGN PATENT DOCUMENTS

| KR | 10-1357800 B1 | 2/2014 |
|----|---------------|--------|
| KR | 10-2017-0004547 A | 1/2017 |
| KR | 10-2017-0004914 A | 1/2017 |

OTHER PUBLICATIONS

Machine translation of KR 101357800 (Year: 2014).*
Machine translation of KR 1020170004914 (Year: 2016).*
Office Action dated Mar. 6, 2019, by the Korean Intellectual Property Office in corresponding Korean Patent Application No. 10-2017-0147608. (42 pages).
Russell, "A Circumplex Model of Affect", Journal of Personality and Social Psychology, 1980, pp. 1161-1178, vol. 39, No. 6, American Psychological Association, Inc.
Tekalp et al., "Face and 2-D Mesh Animation in MPEG-4", Signal Processing: Image Communication, 2000, pp. 387-421, vol. 15, Elsevier Science B.V.
Daugman, "How Iris Recognition Works", IEEE Transactions on Circuits and Systems for Video Technology, Jan. 2004, pp. 21-30, vol. 14, No. 1, IEEE.
Lee et al., "Measuring the Degree of Eyestrain Caused by Watching LCD and PDP Devices", International Journal of Industrial Ergonomics, 2009, pp. 798-806, vol. 39, Elsevier B.V.
Schandry et al., "Event-Related Brain Potentials and the Processing of Cardiac Activity", Biological Psychology 1996, pp. 75-85, vol. 42, Elsevier Science B.V.
Park et al., "Does Visual Fatigue from 3D Displays Affect Autonomic Regulation and Heart Rhythm", International Journal of Psychophysiology, 2014, pp. 42-48, vol. 92, Elsevier B.V.
Park et al., "Evaluation of 3D Cognitive Fatigue using Heart-Brain Synchronization", International Journal of Psychophysiology, 2015, pp. 120-130, vol. 97, Elsevier B.V.
Montoya et al., "Heartbeat Evoked Potentials (HEP): Topography and Influence of Cardiac Awareness and Focus of Attention", Electroencephalography and Clinical Neurophysiology, 1993, pp. 163-172, vol. 88, Elsevier Scientific Publishers Ireland, Ltd.
Janig, "Neurobiology of Visceral Afferent Neurons: Neuroanatomy, Functions, Organ Regulations and Sensations", Biological Psychology, 1996, pp. 29-51, vol. 42, Elsevier Science B.V.
Rau et al., "Baroreceptor Stimulation Alters Cortical Activity", Psychophysiology, 1993, pp. 322-325, vol. 30, Society of Psychophysiological Research.
Hansen et al., "Vagal Influence on Working Memory and Attention", International Journal of Psychophysiology, 2003, pp. 263-274, vol. 48, Elsevier Science B.V.
McCraty et al., The Coherent Heart Heart-Brain Interactions, Psychophysiological Coherence, and the Emergence of System-Wide Order, Integral Review, Dec. 2009, pp. 10-115, vol. 5, No. 2.
Pan et al., "A Real-Time QRS Detection Algorithm", IEEE Transactions on Biomedical Engineering, Mar. 1985, pp. 230-236, vol. BME-32, No. 3, IEEE.
Dunnett, "A Multiple Comparison Procedure for Comparing Several Treatments with a Control", Journal of the American Statistical Association, Dec. 1955, pp. 1096-1121, vol. 50, No. 242, American Statistical Association.
Cohen, Statistical Power Analysis for the Behavioral Sciences, Biometrics, Sep. 1970, pp. 588, vol. 26, No. 3, International Biometric Society.
Office Action (First Office Action) dated Dec. 3, 2019, by the State Intellectual Property Office of People's Republic of China in corresponding Chinese Patent Application No. 201810109055.4 and an English Translation of the Office Action. (Summary of Office Action, 1 page), (20 pages).

* cited by examiner

Cortex: Cognitive function, Performance
Thalamus: Synchronizes cortical activity
AG(Amygdala): Emotional Memory
MD(Medulla): Pressure and ANS regulation
V(x): Central Nervous, X vagal
HVN: Heart Vagal Nervous
HEP: Heartbeat Evoked Potential

METHOD AND SYSTEM FOR DETECTING INFORMATION OF BRAIN-HEART CONNECTIVITY BY USING PUPILLARY VARIATION

CROSS-REFERENCE TO RELATED APPLICATION

This application claims the benefit of Korean Patent Application Nos. 10-2017-0021520, filed on Feb. 17, 2017, and 10-2017-0147608, filed on Nov. 7, 2017, in the Korean Intellectual Property Office, the disclosures of which are incorporated herein in their entirety by reference.

BACKGROUND

1. Field

One or more embodiments relate to a method of detecting physiological information by using a pupillary response, and a system using the method, and more particularly, to method of detecting parameters of brain-heart connectivity from a pupil size variation, and a system using the method.

2. Description of the Related Art

In vital signal monitoring (VSM), physiological information can be acquired by a sensor attached to a human body. Such physiological information includes electrocardiogram (ECG), photo-plethysmograph (PPG), blood pressure (BP), galvanic skin response (GSR), skin temperature (SKT), respiration (RSP) and electroencephalogram (EEG).

The heart and brain are two main organs of the human body and analysis thereof provide the ability to evaluate human behavior and obtain information that may be used in response to events and in medical diagnosis. The VSM may be applicable in various fields such as ubiquitous healthcare (U-healthcare), emotional information and communication technology (e-ICT), human factor and ergonomics (HF&E), human computer interfaces (HCIs), and security systems.

Regarding ECG and EEG, sensors attached to the body are used to measure physiological signals and thus, may cause inconvenience to patients. That is, the human body experiences considerable stress and inconvenience when using sensors to measure such signals. In addition, there are burdens and restrictions with respect to the cost of using the attached sensors and to the movement of the subject, due to attached sensor hardware.

Therefore, VSM technology is required in the measurement of physiological signals by using non-contact, non-invasive, and non-obtrusive methods while providing unfettered movement at low cost.

Recently, VSM technology has been incorporated into wireless wearable devices allowing for the development of portable measuring equipment. These portable devices can measure the heart rate (HR) and RSP by using VSM embedded into accessories such as watches, bracelets, or glasses.

Wearable device technology is predicted to develop from portable devices to "attachable" devices shortly. It is also predicted that attachable devices will be transferred to "eatable" devices.

VSM technology has been developed to measure physiological signals by using non-contact, non-invasive, and non-obtrusive methods that provide unfettered movement at low cost. While VSM will continue to advance technologically, innovative vision-based VSM technology is required to be developed also.

SUMMARY

One or more embodiments include a system and method for inferring and detecting human vital signs by non-invasive and non-obstructive method at low cost.

In detail, one or more embodiments include a system and method for detecting parameters of brain-heart connectivity by using a pupil rhythm or pupillary variation.

Additional aspects will be set forth in part in the description which follows and, in part, will be apparent from the description, or may be learned by practice of the presented embodiments.

According to one or more exemplary embodiments, the method of detecting information of brain-heart connectivity, the method comprises obtaining moving images of a pupil and an electrocardiogram (ECG) signal from a subject; acquiring a pupil size variation (PSV) from the moving images by separating the moving images based on a predetermined time range after R-peak of the ECG signal; extracting signals of a first period and a second period from the PSV; calculating alpha powers of the signals of the first and second periods at predetermined frequencies, respectively.

According to one or more exemplary embodiments, the method further comprises repeating the acquiring a predetermined number of times to obtain a plurality of the PSV; and integrating the plurality of the PSV into a PSV based on a grand average technique.

According to one or more exemplary embodiments, the predetermined time range is between 56 ms to 600 ms.

According to one or more exemplary embodiments, the first period ranges between 56 ms-348 ms after the R-peak.

According to one or more exemplary embodiments, the second period ranges between 248 ms-600 ms after the R-peak.

According to one or more exemplary embodiments, the frequency of the alpha power of the first period is 10 Hz, and the frequency of the alpha power of the second period is 9 Hz or 11 Hz.

According to one or more exemplary embodiments, the first period ranges between 56 ms-348 ms after the R-peak, and the second period ranges between 248 ms-600 ms after the R-peak. According to one or more exemplary embodiments, According to one or more exemplary embodiments, the frequency of the alpha power of the first period is 10 Hz, and the frequency of the alpha power of the second period is 9 Hz or 11 Hz.

According to one or more exemplary embodiments, each of the alpha powers is obtained from a ratio of power of the respective frequency thereof to a total power of a total frequency ranging from 0 Hz to 62.5 Hz.

According to one or more exemplary embodiments, the system adopting the method comprises a video capturing unit configured to capture the moving images of the subject; and a computer architecture based analyzing unit, including analysis tools, configured to process, analyze the moving images, and calculate the alpha powers of the signals of the first and second periods.

BRIEF DESCRIPTION OF THE DRAWINGS

In these and/or other aspects will become apparent and more readily appreciated from the following description of the embodiments, taken in conjunction with the accompanying drawings in which.

DETAILED DESCRIPTION

Figure 1:
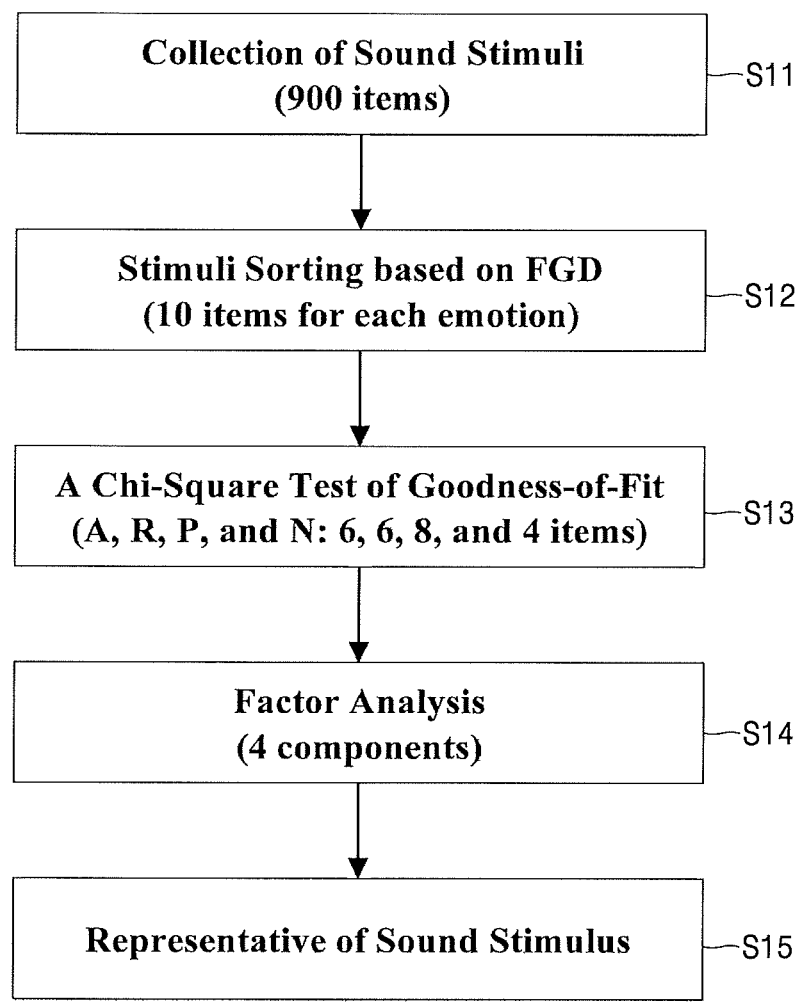
FIG. 1 shows a procedure for selecting a representative of sound stimulus used in an example test, according to one or more embodiments.

In Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, a method and system for inferring and detecting physiological signals according to the present inventive concept is described with reference to the accompanying drawings.

The invention may, however, be embodied in many different forms and should not be construed as being limited to the embodiments set forth herein; rather, these embodiments are provided so that this disclosure will be thorough and complete, and will fully convey the concept of the invention to those skilled in the art. Like reference numerals in the drawings denote like elements. In the drawings, elements and regions are schematically illustrated. Accordingly, the concept of the invention is not limited by the relative sizes or distances shown in the attached drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, numbers, steps, operations, elements, and/or components, but do not preclude the presence or addition of one or more other features, numbers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present application, and will not be interpreted in an overly formal sense unless expressly so defined herein.

The embodiments described below involve processing brain frequency information from pupillary response which is obtained from video information The present invention, which may be sufficiently understood through the embodiments described below, involve extraction brain frequency information from the pupillary response by using a vision system equipped with a video camera such as a webcam without any physical restriction or psychological pressure on the subject, Especially, the pupillary response is detected from the image information and information of brain-heart connectivity is extracted from it.

In the experiment of the present invention, the reliability of the parameters of the brain-heart connectivity extracted from the pupil size variation (PSV) acquired through moving images was compared with the ground truth signal by EEG sensors.

The experiment of the present invention has been performed by video equipment, and computer architecture based analyzing system for processing and analyzing the moving image which includes analysis tools provided by software.

Experimental Stimuli

In order to cause variation of the physiological state, this experiment used sound stimuli based on the Russell's circomplex model (Russell, 1980). The sound stimuli included a plurality of factors, including arousal, relaxation, positive, negative, and neutral sounds. The neutral sound was defined by an absence of acoustic stimulus. The steps for selecting sound stimulus are shown in FIG. 1 and listed as follows:

(S11) Nine hundred sound sources were collected from the broadcast media such as advertisements, dramas, and movies.

(S12) The sound sources were then categorized into four groups (i.e., arousal, relaxation, positive, and negative). Each group was comprised of 10 commonly selected items based on a focus group discussion for a total of forty sound stimuli.

(S13) These stimuli were used to conduct surveys for suitability for each emotion (i.e., A: arousal, R: relaxation, P: positive, and N: negative) based on data gathered from 150 subjects that were evenly split into 75 males and 75 females. The mean age was 27.36 years±1.66 years. A subjective evaluation was required to select each item for the four factors, which could result in duplicates of one or more of the items.

(S14) A chi-square test for goodness-of-fit was performed to determine whether each emotion sound was equally preferred. Preference for each emotion sound was equally distributed in the population (arousal: 6 items, relaxation: 6 items, positive: 8 items, and negative: 4 items) as shown in Table 1.

Table 1 shows the chi-square test results for goodness-of-fit in which the items selected for each emotion are based on comparisons of observation and expectation values.

TABLE 1

|  | N | Chi-Square | Sig. |
|---|---|---|---|
| Arousal | | | |
| arousal 1 | 150 | 83.867 | .000 |
| arousal 2 | 150 | 45.573 | .000 |
| arousal 3 | 150 | 58.200 | .000 |
| arousal 5 | 150 | 83.440 | .000 |
| arousal 9 | 150 | 10.467 | .000 |
| arousal 10 | 150 | 70.427 | .000 |
| Relaxation | | | |
| relaxation 1 | 150 | 131.120 | .000 |
| relaxation 2 | 150 | 163.227 | .000 |
| relaxation 5 | 150 | 80.720 | .000 |
| relaxation 6 | 150 | 11.640 | .000 |
| relaxation 7 | 150 | 82.587 | .000 |
| relaxation 10 | 150 | 228.933 | .000 |
| Positive | | | |
| positive 2 | 150 | 35.040 | .000 |
| positive 3 | 150 | 90.533 | .000 |
| positive 4 | 150 | 101.920 | .000 |
| positive 5 | 150 | 66.040 | .000 |
| positive 7 | 150 | 143.813 | .000 |
| positive 8 | 150 | 128.027 | .000 |
| positive 9 | 150 | 47.013 | .000 |
| positive 10 | 150 | 138.053 | .000 |
| Negative | | | |
| negative 1 | 150 | 119.920 | .000 |
| negative 2 | 150 | 59.440 | .000 |
| negative 5 | 150 | 117.360 | .000 |
| negative 9 | 150 | 62.080 | .000 |

Resurveys of the sound stimuli were conducted for relation to each emotion from the 150 subjects by using a seven-point scale based on 1 indicating strong disagreement to 7 indicating strong agreement.

Valid sounds relating to each emotion were analyzed using PCA (Principal Component Analysis) based on Varimax (orthogonal) rotation. The analysis yielded four factors explaining of the variance for the entire set of variables. Following the analysis result, representative sound stimuli for each emotion were derived, as shown in Table 2.

In Table 2, the bold type is the same factor, the blur character is the communalities<0.5, and the thick, light gray lettering with shading in the background represents the representative acoustic stimulus for each emotion.

TABLE 2

|  | Component | | | |
|---|---|---|---|---|
|  | 1 | 2 | 3 | 4 |
| *positive9* | *.812* | *.065* | *.021* | *-.033* |
| arousal 9 | .751 | -.353 | -.157 | .107 |
| relaxation 7 | .717 | .355 | .084 | .133 |
| positive 2 | .531 | -.202 | .203 | .107 |
| positive 3 | -.528 | .222 | .406 | -.003 |
| positive 8 | .520 | .142 | .161 | .074 |
| *relaxation2* | *.192* | *.684* | *.109* | *.004* |
| relaxation 1 | .028 | .649 | .168 | -.147 |
| relaxation 5 | -.290 | .629 | -.008 | .132 |

TABLE 2-continued

|  | Component | | | |
|---|---|---|---|---|
|  | 1 | 2 | 3 | 4 |
| relaxation 6 | .025 | .628 | -.061 | .107 |
| relaxation 10 | .052 | .569 | -.320 | -.187 |
| arousal 10 | -.201 | .529 | -.111 | .409 |
| *positive 10* | *-.145* | *.424* | *.342* | *-.020* |
| *negative1* | *-.257* | *-.009* | *.672* | *.123* |
| positive 4 | .111 | .096 | .608 | -.185 |
| negative 2 | -.503 | .108 | .580 | .104 |
| negative 9 | .289 | -.252 | .566 | -.051 |
| negative 5 | .216 | -.232 | .528 | -.094 |
| positive 5 | .377 | .014 | .439 | -.019 |
| positive 7 | .002 | .193 | .403 | .128 |
| *arousal1* | *-.158* | *.209* | *-.042* | *.774* |
| arousal 2 | .129 | -.049 | .015 | .765 |
| arousal 5 | .210 | -.043 | .097 | .672 |
| arousal 3 | .566 | -.159 | -.140 | .617 |

Experimental Procedure

In Seventy undergraduate volunteers of both genders, evenly split between males and females, ranging in age from 20 to 30 years old with a mean of 24.52 years±0.64 years participated in this experiment. All subjects had normal or corrected-to-normal vision (i.e., over 0.8), and no family or medical history of disease involving visual function, cardiovascular system, or the central nervous system. Informed written consent was obtained from each subject prior to the study. This experimental study was approved by the Institutional Review Board of Sangmyung University, Seoul, South Korea (2015 Aug. 1).

The experiment was composed of two trials where each trail was conducted for a duration of 5 min. The first trail was based on the movelessness condition (MNC), which involves not moving or speaking. The second trial was based on the natural movement condition (NMC) involving simple conversations and slight movements. Participants repeatedly conducted the two trials and the order was randomized across the subjects. In order to verify the difference of movement between the two conditions, this experiment quantitatively measured the amount of movement during the experiment by using webcam images of each subject. In the present invention, the moving image may include at least one pupil, that is, one pupil or both pupils image.

The images were recorded at 30 frames per second (fps) with a resolution of 1920×1080 by using a HD Pro C920 camera from Logitech Inc. The movement measured the upper body and face based on MPEG-4 (Tekalp and Ostermann, 2000; JPandzic and Forchheimer, 2002). The movement in the upper body was extracted from the whole image based on frame differences. The upper body line was not tracking because the background was stationary.

The movement in the face was extracted from 84 MPEG-4 animation points based on frame differences by using visage SDK 7.4 software from Visage Technologies Inc. All movement data used the mean value from each subject during the experiment and was compared to the difference of movement between the two trails, as shown in FIG. 2.

Figure 2:
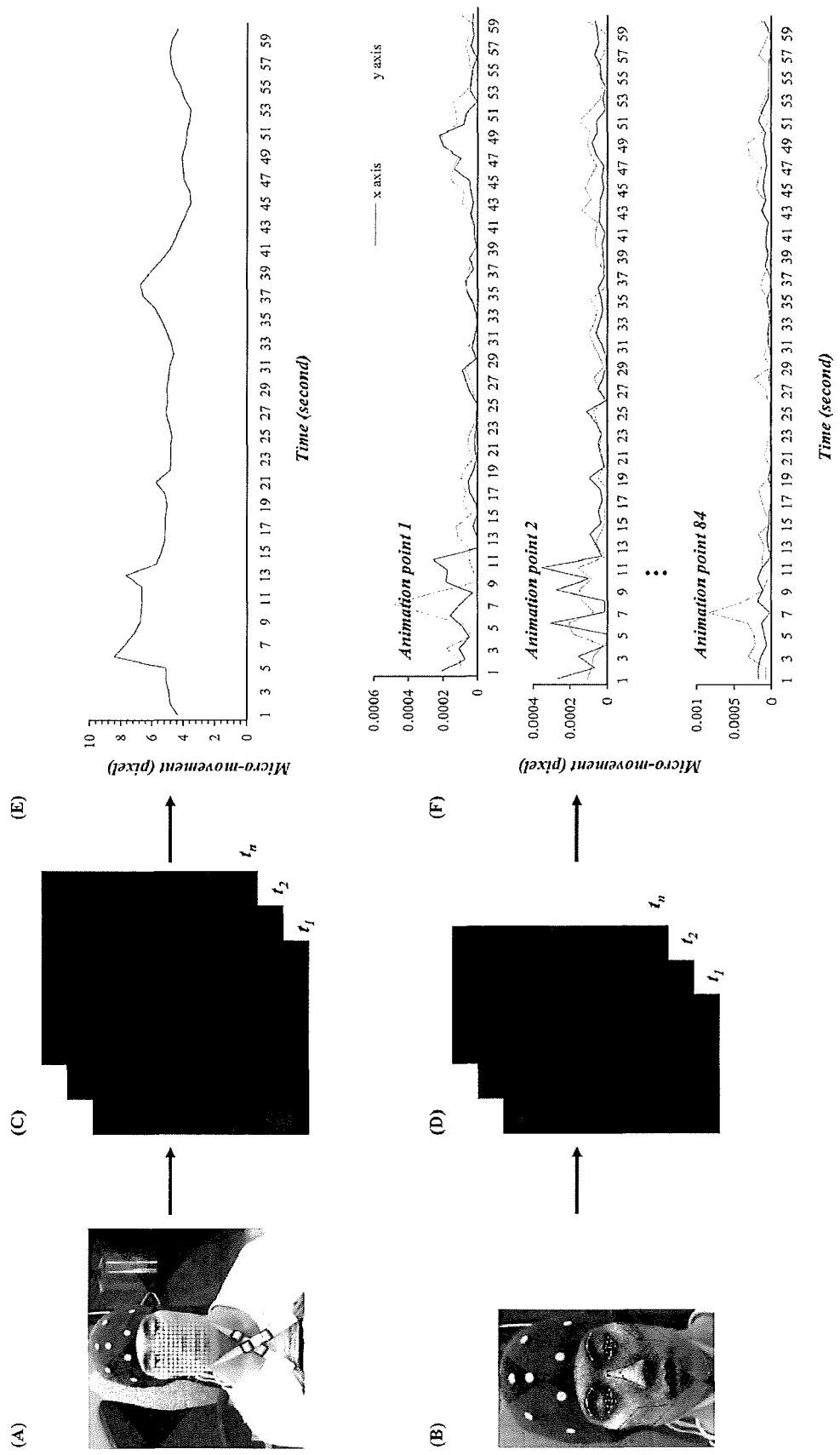
FIG. 2 shows an experimental procedure for measuring the amount of movement in an upper body, according to one or more embodiments.

FIG. 2 shows an example of measuring the amount of motion of the subject's upper body in a state of the face is located at the intersection of the X axis and the Y axis, In FIG. 2, (A) is an upper body image, (B) is a tracked face image at 84 MPEG-4 animation points, (C) and (D) shows the difference between before and after frames, (E) is a movement signal from the upper body, and (F) shows movement signals from 84 MPEG-4 animation points.

In order to cause the variation of physiological states, sound stimuli were presented to the participants during the trails. Each sound stimulus was randomly presented for 1 min for a total of five stimuli over the 5 min trial. A reference stimulus was presented for 3 min prior to the initiation of the task. The detailed experimental procedure is shown in FIG. 3.

Figure 3:
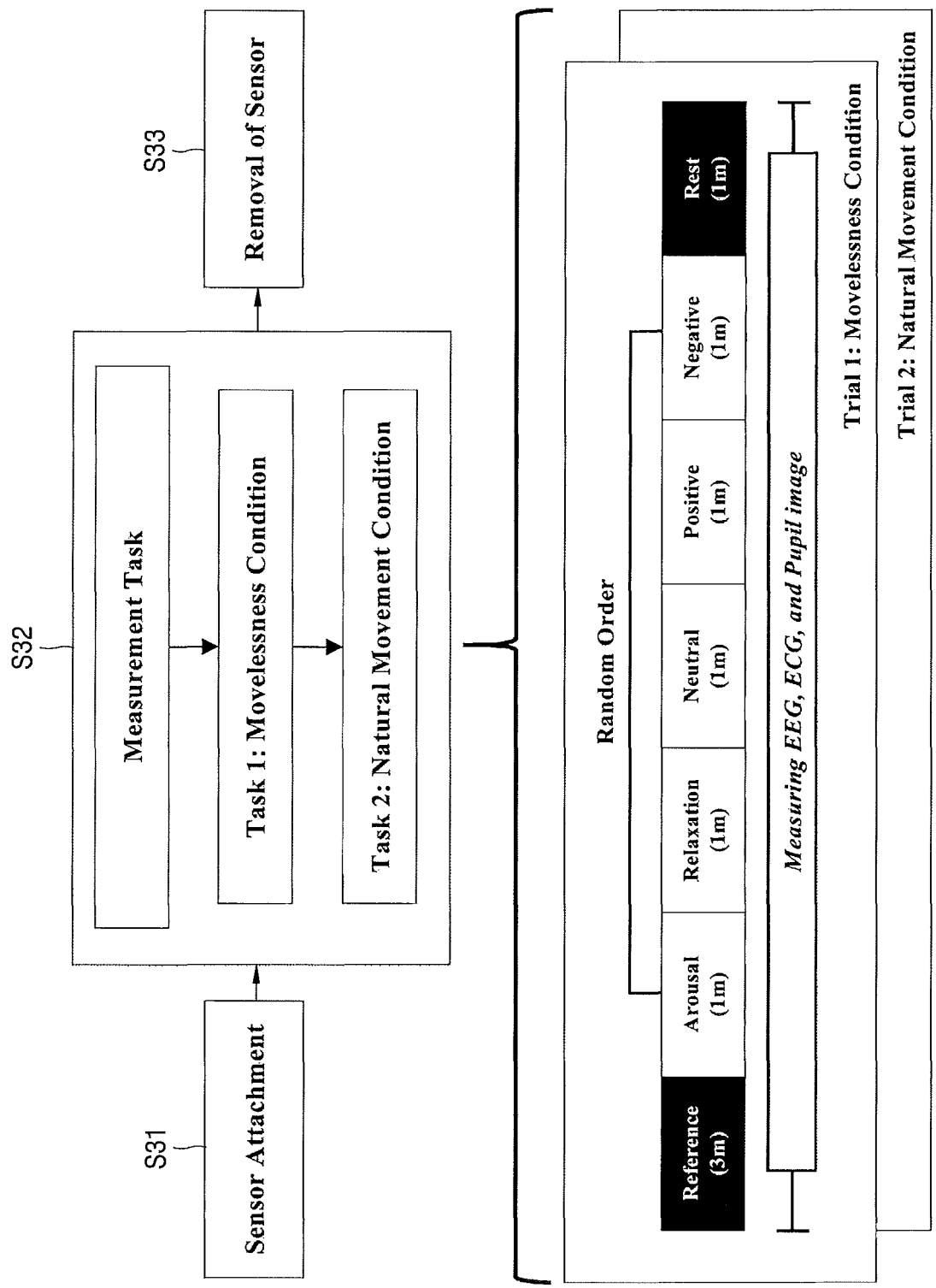
FIG. 3 is a block diagram for explaining an experimental procedure, according to one or embodiments.

The experimental procedure includes the sensor attachment S31, the measurement task S32 and the sensor removal S33 as shown in FIG. 3, and the measurement task S32 proceed as follows.

The experiment was conducted indoors with varying illumination caused by sunlight entering through the windows. The participants gazed at a black wall at a distance of 1.5 m while sitting in a comfortable chair. Sound stimuli were equally presented in both the trials by using earphones. The subjects were asked to constrict their movements and speaking during the movelessness trial (MNC). However, the natural movement trial (NMC) involved a simple conversation and slight movement by the subjects. The subjects were asked to introduce themselves to another person as part of the conversation for sound stimuli thereby involving feelings and thinking of the sound stimuli. During the experiment, EEG, ECG signal and pupil image data were obtained.

EEG signals were recorded at a 500 Hz sampling rate from nineteen channels (FP1, FP2, F3, Fz, F4, F7, F8, C3, Cz, C4, T7 (T3), T8 (T4), P7 (T5), P8 (T6), P3, Pz, P4, O1, and O2 regions) based on the international 10-20 system (ground: FAz, reference: average between electrodes on the two ears, and DC level: 0 Hz-150 Hz). The electrode impedance was kept below 3 kΩ. EEG signals were recorded at a 500 Hz sampling rate using a Mitsar-EEG 202 Machine.

ECG signals were sampled and recorded at a 500 Hz sampling rate through one channel with the lead-I method by an amplifier system including ECG 100C amplifiers and a MP100 power supply from BIOPAC System Inc. The ECG signals were digitalized by a NI-DAQ-Pad 9205 of National Instrument Inc.

Pupil images were recorded at 125 fps with a resolution of 960×400 by GS3-U3-23S6M-C infrared camera from Point Grey Research Inc.

Hereinafter, a method for extracting or constructing (recovering) vital signs from a pupillary response will be described.

Extraction of a Pupillary Response

Figure 4:
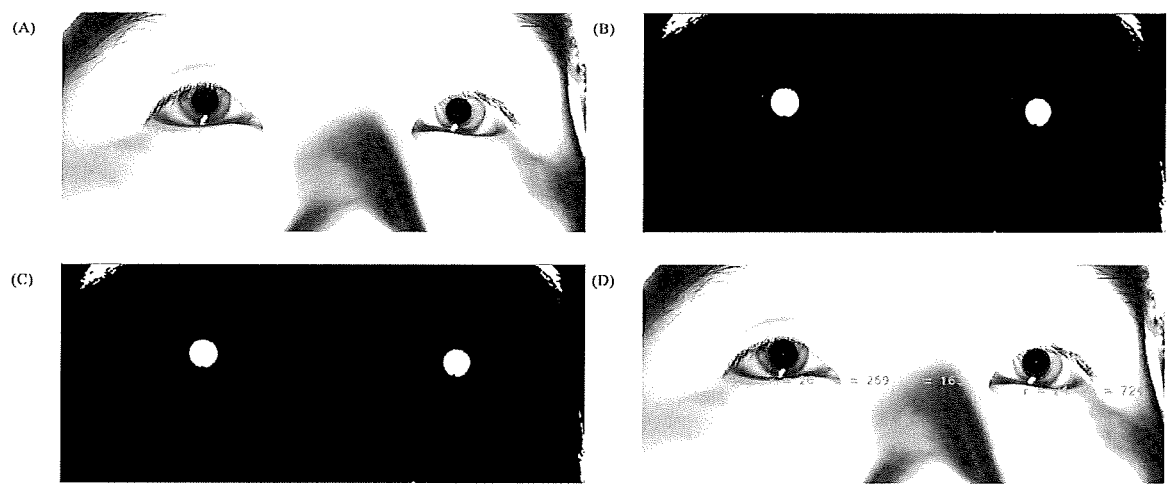
FIG. 4 shows a procedure for detecting a pupil region, according to one or more embodiments.

The pupil detection procedure acquires moving images using the infrared video camera system as shown in FIG. 12, and then requires a specific image processing procedure The pupil detection procedure required following certain image processing steps since the images were captured using an infrared video camera, as shown in FIG. 4.

FIG. 4 shows a process of detecting a pupil region from the face image of a subject. In FIG. 4, (A) shows an input image (gray scale) obtained from a subject, (B) shows a binarized image based on an auto threshold, (C) shows pupil positions by the circular edge detection, and (D) shows the real-time detection result of the pupil region including the information about the center coordinates and the diameter of the pupil region. The threshold value was defined by a linear regression model that used a brightness value of the whole image, as shown in Equation 1.

$$\text{Threshold} = (-0.418 \times B_{mean} + 1.051 \times B_{max}) + 7.973$$

$B$=Brightness value  <Equation 1>

The next step to determine the pupil position involved processing the binary image by using a circular edge detection algorithm, as shown in Equation 2 (Daugman, 2004; Lee et al., 2009).

$$\text{Max}_{(r,x_0,y_0)} \left| G\sigma(r) * \frac{\delta}{\delta r} \oint_{r,x_0,y_0} \frac{I(x,y)}{2\pi r} ds \right| \quad \text{<Equation 2>}$$

$I(x,y)$=a grey level at the (x,y) position
$(x_0,y_0)$=center position of pupil
$r$=radius of pupil In case that multiple pupil positions were selected, the reflected light caused by the infrared lamp was used. Then an accurate pupil position was obtained, including centroid coordinates (x, y) and a diameter.

Pupil diameter data (signal) was resampled at a frequency range of 1 Hz-30 Hz, as shown in Equation 3. The resampling procedure for the pupil diameter data involved a sampling rate of 30 data points, which then calculated the mean value during 1-s intervals by using a common sliding moving average technique (i.e., a window size of 1 second and a resolution of 1 second). However, non-tracked pupil diameter data caused by the eye closing was not involved in the resampling procedure.

$$(SMA_m)_{x+n} = \left( \frac{\sum_{i=1}^{m} P_i}{m} \right)_x, \left( \frac{\sum_{i=1}^{m} P_i}{m} \right)_{x+1}, \ldots, \left( \frac{\sum_{i=1}^{m} P_i}{m} \right)_{x+n} \quad \text{<Equation 3>}$$

SMA=sliding moving average
P=pupil diameter

Detecting Heartbeat Evoked Potential Index

The detection of the heartbeat evoked potential (HEP) index is now described. The HEP includes alpha activity of first and second components of the HEP which is extracted or determined from the pupillary response. The HEP is a phenomenon related to change of brain alpha activity which can be caused by heart rhythm and blood flow (Schandry and Montoya, 1996; Park et al., 2014; Park et al., 2015).

The major organs of human body, such as the heart, have visceral neurons known as vagus nervous which transmits cardiac information from the heart to the brain through the visceral afferent pathway. (Montoya et al., 1993; Park et al., 2014; Park et al., 2015). The afferent information in the heart is integrated at the nucleus tractus solitarius and then is transmitted to mid-brain areas such as the hypothalamus, thalamus, and amygdala (Janig, 1996; Park et al., 2014; Park et al., 2015). The mid-brain area communicates with the neocortex specifically with the prefrontal brain areas (Fuster, 1980; Nauta and Feirtag, 1986; Nieuwenhuys et al., 2007; Park et al., 2015). This phenomenon is closely related to cognitive functions, human performance, emotional state (Rau et al., 1993; Hansen et al., 2003; McCraty et al., 2009; Park et al., 2015).

Figure 5:
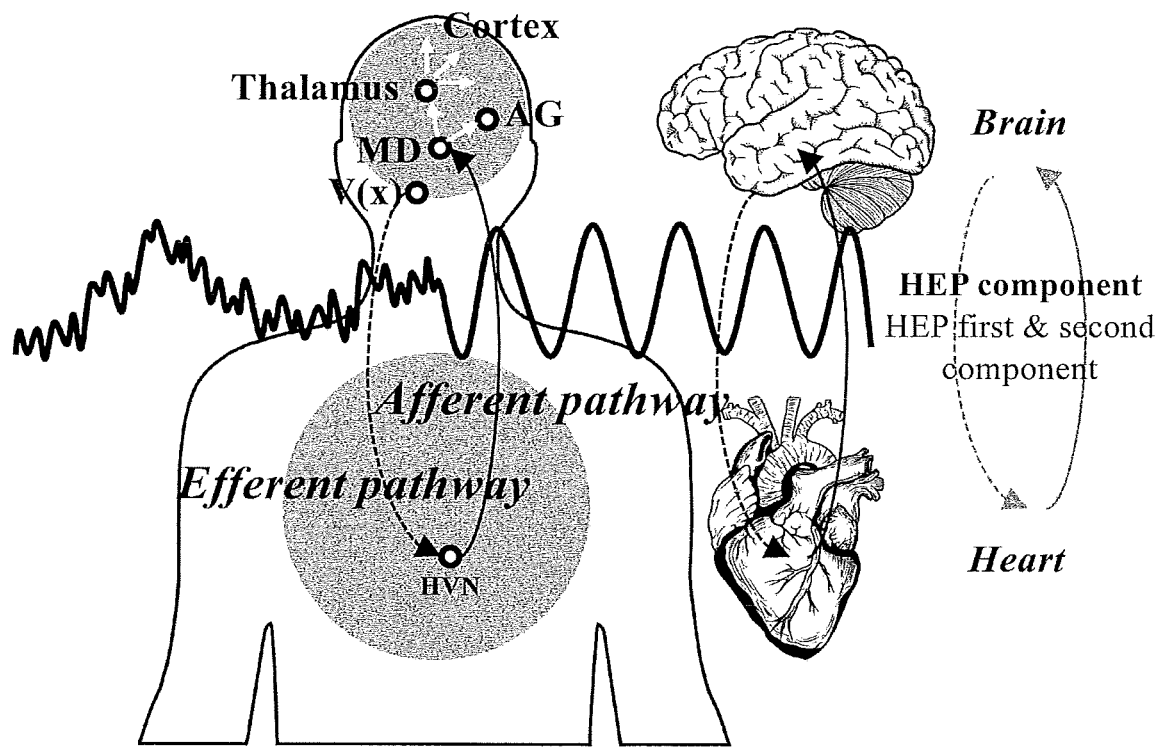
FIG. 5 schematically explains a theory of brain-heart connectivity, according to one or more embodiments.

FIG. 5 schematically explains a theory of the brain-heart connectivity. As shown in FIG. 5, heartbeat evoked potential is focused on the vagus nervous in heart by the neurological circulation of afferent and efferent pathway.

Figure 6:
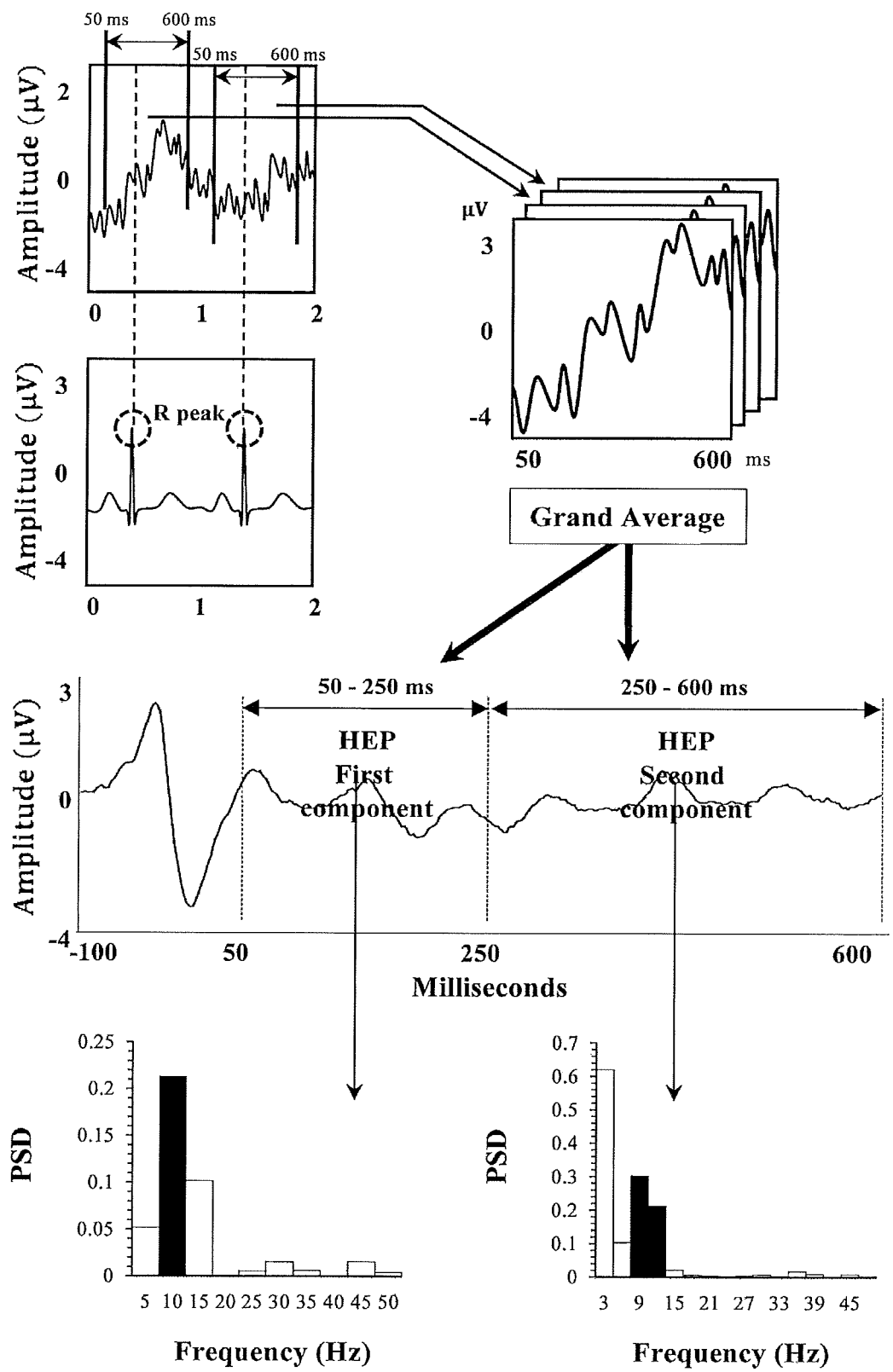
FIG. 6 shows an extraction process of a heartbeat evoked potential (HEP) waveform signal, according to one or more embodiments.

The HEP is divided into two periods. The first HEP period is the mean time interval required to transmit the cardiac afferent information from the heart to the brain and is 50 ms-250 ms after the R-peak. To increase the alpha power at 10 Hz means, the activation of the communication between the heart and the brain is increased. The second period of the HEP reflects the time interval required to transmit the cardiac blood pressure wave from the heart to the brain and is 250 ms-600 ms after the R-peak. To increase the alpha power at 9 Hz and 12 Hz, the means higher cognitive processing is occurred based on the sensory input. This phenomenon is concerned with brain alpha rhythm in prefrontal cortex such as FP1 and FP2 (Wölk et al., 1989; McCraty et al., 2009; Park et al., 2015). The HEP waveform is extracted by grand average technique of all trial signals based on the R-peak value. The quantification of the alpha power is obtained using by FFT analysis of each component of the first and second period, as shown in FIG. 6 (Wölk et al., 1989; McCraty et al., 2009; Park et al., 2015).

FIG. 6 shows a extraction progress of HEP waveform signal including a first and second components of HEP from the pupillary response. The signal of the pupil diameter at 125 fps was calculated from the PSV by using the frame difference of the pupil diameter, as shown in Equation (4).

$$PSV = \frac{\sum_{i=1}^{n} |P_{n+1} - P_n|}{n} \qquad \langle \text{Equation 4} \rangle$$

PSV=pupil size variation
P=pupil diameter

The PSV data was separated based on the R-peak signals from the ECG signal in the range of 56 ms-600 ms after R-peak. This procedure was repeated over the 100 trials. All trial signals were integrated into the one signal (PSV data) by using the grand average technique (Park et al., 2015). This signal was divided into the first period represented by the time frame of 56 ms-248 ms after the R-peak, and the second period represented by the time frame of 256 ms-600 ms after the R-peak. Each period was processed using FFT analysis, as shown in Equation (5).

$$X_k = \sum_{n=0}^{N-1} x_n e^{-i 2\pi k \frac{n}{N}} \qquad \langle \text{Equation 5} \rangle$$

$$k = 0, \ldots, N-1$$

The alpha power of the first period (i.e., 10 Hz) and second period (i.e., 9 Hz and 11 Hz) periods was calculated from the ratio of alpha power to total power of a total frequency band ranging from 0 Hz to 62.5 Hz) as shown in Equation (6).

$$FAP = \frac{A\ \text{power (10 Hz)}}{\text{Total Power}} \times 100$$

$$SAP = \frac{A\ \text{power (9, 11 Hz)}}{\text{Total Power}} \times 100$$

FAP=A power of HBP 1st period
SAP=A power of HBP 2nd period

The EEG signals in the FP1 and FP2 regions were extracted from a specific range of 50 ms-600 ms after the R-peak based on the R-peak location. The R-peak was detected from ECG signals by using the QRS detection algorithm (Pan and Tompkins, 1985). All trials extracted EEG signals that were processed by the grand average (Park et al., 2015). The FP1 and FP2 signals were integrated into the HEP waveform signal by using the grand average. The HEP waveform was divided into the first period of 50 ms-250 ms after the R-peak and the second period of 250 ms-600 ms after the R-peak where each period was processed using FFT analysis, as shown in Equation (5). The alpha power of the first and second periods was calculated from the ratio between the alpha power and total power in the range of 0 Hz-250 Hz as shown in Equation (6).

Figure 7:
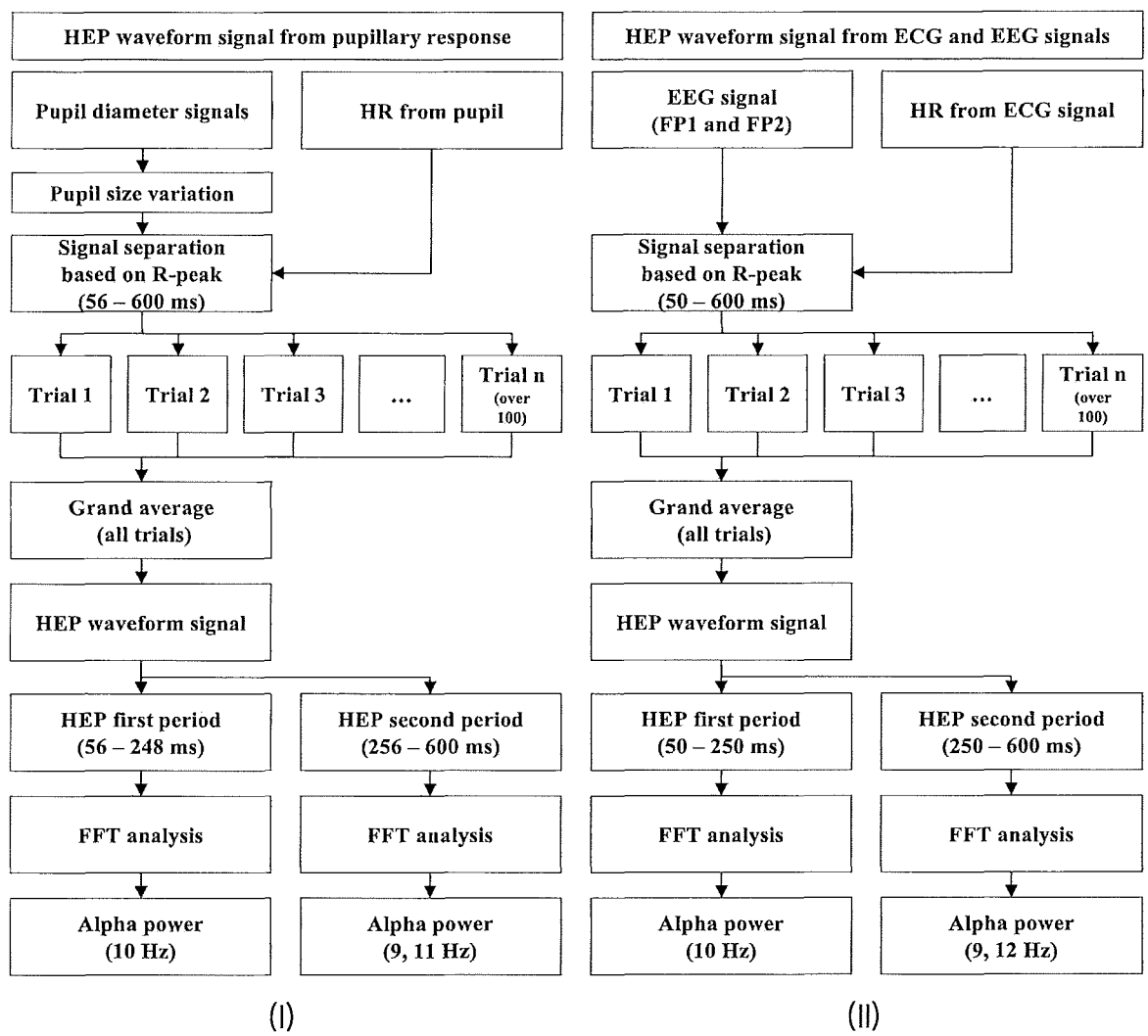
FIG. 7 shows procedures for processing the HEP waveform signals, according to one or more embodiments.

The detailed procedures for processing the HEP waveform signals based each of the pupillary response, and EEG/ECG signals are shown in FIG. 7. In FIG. 7, (I) shows a procedure for HEP waveform signal from the pupillary response, and (II) shows a procedure for HEP waveform from the ECG and EEG signals.

Result

The pupillary response was processed to extract the vital signs from the cardiac time domain index, cardiac frequency domain index, EEG spectral index, and the HEP index of the test subjects. These components were compared with each index from the sensor signals (i.e., ground truth) based on correlation coefficient (r) and mean error value (ME). The data was analyzed in both MNC and NMC for the test subjects.

To verify the difference of the amount movement between the two conditions of MNC and NMC, the movement data was quantitatively analyzed. The movement data was a normal distribution based on a normality test of probability-value (p)>0.05, and from an independent t-test. A Bonferroni correction was performed for the derived statistical significances (Dunnett, 1955). The statistical significance level was controlled based on the number of each individual hypothesis (i.e., $\alpha=0.05/n$). The statistical significant level of the movement data sat up 0.0167 (upper body, X and Y axis in face, $\alpha=0.05/3$). The effect size based on Cohen's d was also calculated to confirm practical significance. In Cohen's d, standard values of 0.10, 0.25, and 0.40 for effect size are generally regarded as small, medium, and large, respectively (Cohen, 2013).

Figure 8:
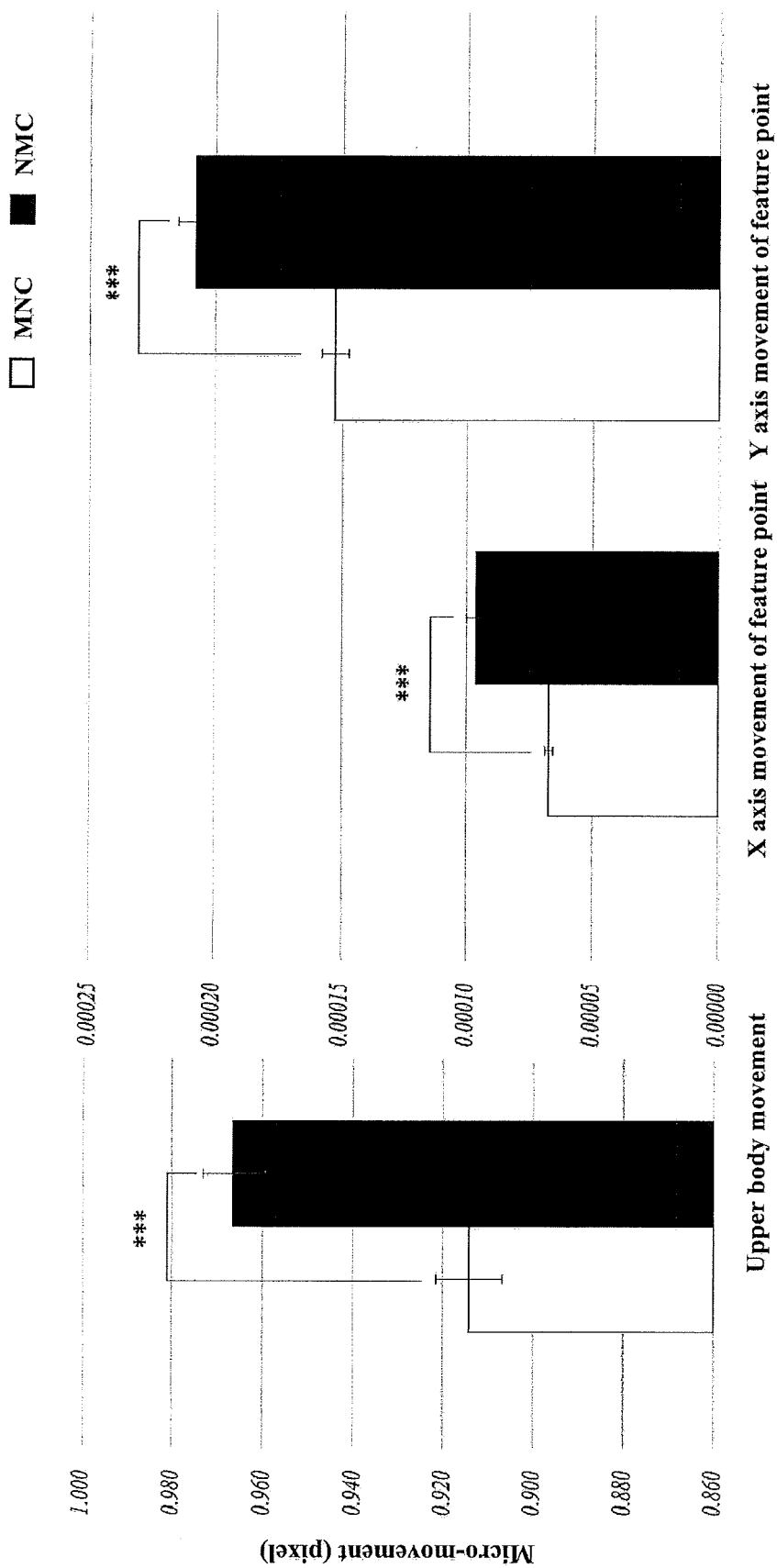
FIG. 8 shows averages of amounts of movement in an upper body.

FIG. 8 shows averages of amount movement in upper body, X and Y axis in face for MNC and NMC (n=140, *** p<0.001). Table 3 shows all subjects data of amount movement in upper body, X and Y axis in face for MNC and NMC.

Referring FIG. 8 and Table 3 according to the analysis, the amount of movement in MNC (upper body, X and Y axis for the face) was significantly increased compared to the NMC for the upper body (t(138)=−5.121, p=0.000, Cohen's d=1.366 with large effect size), X axis for the face (t(138)=−6.801, p=0.000, Cohen's d=1.158 with large effect size), and Y axis for the face (t(138)=−6.255, p=0.000, Cohen's d=1.118 with large effect size).

TABLE 3

| | Movelessness Condition (MNC) | | | Natural Movement Condition (NMC) | | |
|---|---|---|---|---|---|---|
| Subjects | Upper body | X axis | Y axis | Upper body | X axis | Y axis |
| S1 | 0.972675 | 0.000073 | 0.000158 | 1.003305 | 0.000117 | 0.000237 |
| S2 | 0.961020 | 0.000081 | 0.000170 | 1.002237 | 0.000101 | 0.000243 |
| S3 | 0.942111 | 0.000071 | 0.000206 | 0.945477 | 0.000081 | 0.000220 |
| S4 | 0.955444 | 0.000067 | 0.000189 | 0.960506 | 0.000072 | 0.000191 |
| S5 | 0.931979 | 0.000056 | 0.000106 | 0.972033 | 0.000070 | 0.000153 |
| S6 | 0.910416 | 0.000057 | 0.000103 | 0.999692 | 0.000086 | 0.000174 |
| S7 | 0.862268 | 0.000055 | 0.000216 | 0.867949 | 0.000071 | 0.000249 |
| S8 | 0.832109 | 0.000056 | 0.000182 | 0.884868 | 0.000068 | 0.000277 |
| S9 | 0.890771 | 0.000099 | 0.000188 | 0.890783 | 0.000099 | 0.000242 |
| S10 | 0.869373 | 0.000073 | 0.000168 | 0.872451 | 0.000089 | 0.000206 |
| S11 | 0.908724 | 0.000057 | 0.000128 | 0.963280 | 0.000102 | 0.000187 |
| S12 | 0.954168 | 0.000091 | 0.000180 | 0.964322 | 0.000181 | 0.000190 |
| S13 | 0.846164 | 0.000070 | 0.000144 | 0.917798 | 0.000079 | 0.000172 |
| S14 | 0.953219 | 0.000062 | 0.000116 | 1.024050 | 0.000093 | 0.000185 |
| S15 | 0.936300 | 0.000068 | 0.000202 | 0.952505 | 0.000101 | 0.000287 |
| S16 | 0.943040 | 0.000077 | 0.000220 | 0.958412 | 0.000106 | 0.000308 |
| S17 | 0.852292 | 0.000099 | 0.000199 | 0.901039 | 0.000077 | 0.000310 |
| S18 | 0.901182 | 0.000082 | 0.000278 | 0.920493 | 0.000084 | 0.000262 |
| S19 | 0.943810 | 0.000075 | 0.000156 | 0.974675 | 0.000099 | 0.000386 |
| S20 | 0.988983 | 0.000070 | 0.000162 | 1.029716 | 0.000175 | 0.000184 |
| S21 | 0.952451 | 0.000065 | 0.000102 | 1.005191 | 0.000081 | 0.000141 |
| S22 | 0.965017 | 0.000064 | 0.000099 | 0.999090 | 0.000183 | 0.000150 |
| S23 | 1.068848 | 0.000101 | 0.000200 | 1.090858 | 0.000108 | 0.000255 |
| S24 | 0.993841 | 0.000092 | 0.000184 | 1.052424 | 0.000111 | 0.000247 |
| S25 | 0.883615 | 0.000064 | 0.000258 | 0.913927 | 0.000077 | 0.000283 |
| S26 | 0.870531 | 0.000051 | 0.000221 | 0.906540 | 0.000074 | 0.000252 |
| S27 | 0.955718 | 0.000064 | 0.000126 | 0.963460 | 0.000071 | 0.000169 |
| S28 | 0.968524 | 0.000061 | 0.000142 | 0.985782 | 0.000075 | 0.000184 |
| S29 | 0.794718 | 0.000067 | 0.000119 | 0.918873 | 0.000074 | 0.000136 |
| S30 | 0.817818 | 0.000064 | 0.000105 | 0.914591 | 0.000073 | 0.000148 |
| S31 | 0.937005 | 0.000053 | 0.000138 | 0.979654 | 0.000080 | 0.000203 |
| S32 | 0.974895 | 0.000067 | 0.000204 | 1.011137 | 0.000072 | 0.000215 |
| S33 | 0.877308 | 0.000073 | 0.000134 | 0.899194 | 0.000087 | 0.000196 |
| S34 | 0.867672 | 0.000063 | 0.000127 | 0.894298 | 0.000077 | 0.000188 |
| S35 | 0.948874 | 0.000099 | 0.000182 | 0.952532 | 0.000105 | 0.000217 |
| S36 | 0.968912 | 0.000109 | 0.000217 | 1.020322 | 0.000115 | 0.000240 |
| S37 | 0.811181 | 0.000063 | 0.000204 | 0.964774 | 0.000071 | 0.000244 |
| S38 | 0.921204 | 0.000061 | 0.000160 | 0.966262 | 0.000071 | 0.000213 |
| S39 | 0.907618 | 0.000060 | 0.000151 | 0.951832 | 0.000076 | 0.000188 |
| S40 | 0.907953 | 0.000061 | 0.000169 | 0.920784 | 0.000071 | 0.000188 |
| S41 | 0.907145 | 0.000055 | 0.000151 | 0.937417 | 0.000171 | 0.000196 |
| S42 | 0.909996 | 0.000055 | 0.000163 | 0.995645 | 0.000072 | 0.000222 |
| S43 | 0.940886 | 0.000061 | 0.000137 | 0.971473 | 0.000082 | 0.000188 |
| S44 | 0.979163 | 0.000059 | 0.000127 | 1.058006 | 0.000184 | 0.000244 |
| S45 | 0.946343 | 0.000056 | 0.000109 | 1.029439 | 0.000082 | 0.000156 |
| S46 | 0.951810 | 0.000061 | 0.000154 | 0.977621 | 0.000087 | 0.000256 |
| S47 | 0.809073 | 0.000060 | 0.000147 | 0.961375 | 0.000065 | 0.000252 |
| S48 | 0.961124 | 0.000073 | 0.000176 | 0.997457 | 0.000083 | 0.000189 |
| S49 | 0.994281 | 0.000074 | 0.000172 | 1.020115 | 0.000094 | 0.000222 |
| S50 | 0.853841 | 0.000075 | 0.000194 | 0.978026 | 0.000104 | 0.000247 |
| S51 | 0.818171 | 0.000059 | 0.000168 | 0.850567 | 0.000091 | 0.000255 |
| S52 | 0.845488 | 0.000072 | 0.000134 | 0.895100 | 0.000105 | 0.000293 |
| S53 | 0.899975 | 0.000081 | 0.000150 | 0.967366 | 0.000094 | 0.000179 |
| S54 | 0.819878 | 0.000057 | 0.000106 | 0.907099 | 0.000108 | 0.000193 |
| S55 | 0.824809 | 0.000061 | 0.000119 | 0.854062 | 0.000062 | 0.000125 |
| S56 | 0.829834 | 0.000067 | 0.000126 | 0.915019 | 0.000169 | 0.000157 |
| S57 | 0.836302 | 0.000066 | 0.000126 | 0.892036 | 0.000083 | 0.000172 |
| S58 | 0.876029 | 0.000065 | 0.000155 | 0.988827 | 0.000186 | 0.000163 |
| S59 | 0.876581 | 0.000065 | 0.000149 | 0.924143 | 0.000117 | 0.000296 |
| S60 | 0.881068 | 0.000101 | 0.000252 | 1.063924 | 0.000109 | 0.000381 |
| S61 | 0.880455 | 0.000055 | 0.000093 | 1.007333 | 0.000080 | 0.000190 |
| S62 | 0.900065 | 0.000055 | 0.000087 | 1.028052 | 0.000076 | 0.000176 |
| S63 | 1.045809 | 0.000056 | 0.000102 | 1.061254 | 0.000096 | 0.000161 |
| S64 | 1.067929 | 0.000052 | 0.000105 | 1.070771 | 0.000111 | 0.000162 |
| S65 | 0.949971 | 0.000055 | 0.000101 | 1.004960 | 0.000068 | 0.000143 |
| S66 | 0.964054 | 0.000053 | 0.000093 | 1.068673 | 0.000169 | 0.000140 |
| S67 | 0.828268 | 0.000054 | 0.000082 | 0.886462 | 0.000061 | 0.000117 |
| S68 | 0.922679 | 0.000049 | 0.000079 | 0.945291 | 0.000061 | 0.000102 |
| S69 | 0.946723 | 0.000063 | 0.000112 | 1.069926 | 0.000114 | 0.000119 |
| S70 | 0.977655 | 0.000064 | 0.000113 | 0.999438 | 0.000065 | 0.000119 |
| mean | 0.914217 | 0.000067 | 0.000153 | 0.966343 | 0.000096 | 0.000208 |
| SD | 0.061596 | 0.000014 | 0.000044 | 0.057911 | 0.000033 | 0.000058 |

The HEP index for heart-brain synchronization, the alpha activity of the first and second HEP periods, was extracted from the pupillary response. These components were compared with the HEP index from the EEG and ECG signals (i.e., ground truth).

This research was able to determine the HEP alpha activity for the first and second periods from the pupillary response by the synchronization between the cardiac and brain rhythms. The alpha activity of the first period within the range of 56 ms-248 ms in the HEP waveform from the pupillary response was synchronized with the alpha activity from the first period within the range or 50 ms-250 ms in HEP waveform from the ECG and EEG signal. The alpha activity of the second period within the range of 256 ms-600 ms in the HEP waveform from the pupillary response was synchronized with the alpha activity of the first period in the range of 250 ms-600 ms in the HEP waveform from the ECG and EEG signal.

Figure 9:
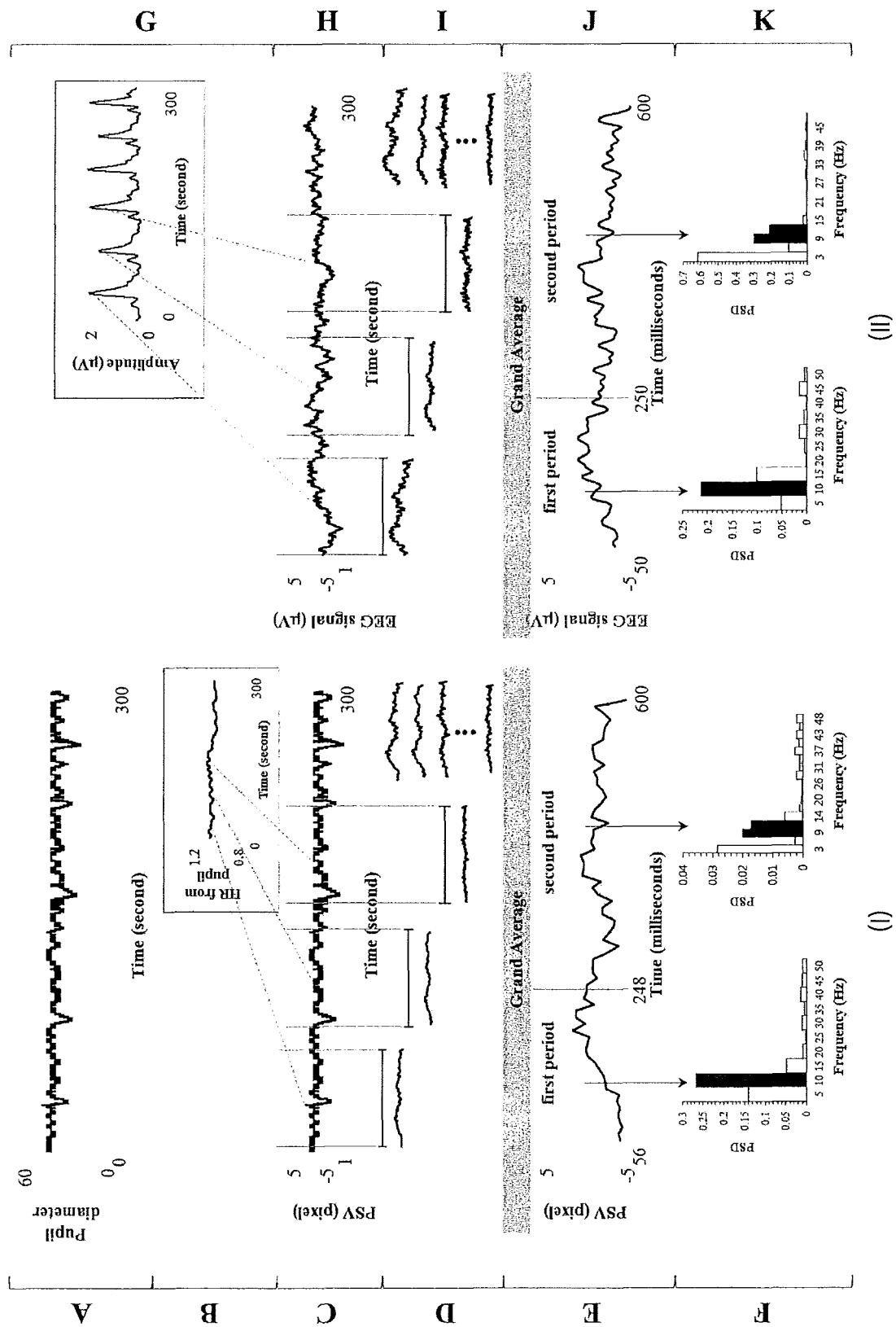
FIG. 9 shows experimental procedures for detecting an HEP index from a pupillary response and EEG signals, according to one or more embodiments.

FIG. 9 shows exemplary processes of extracting the HEP indexes from each of the pupillary response (I) and ECG signals (II). In FIG. 9, (A) shows a pupil diameter signal (pupillary response), (B) shows a heart rate (HR) signal from the pupillary response, (C) shows a pupil size variation, (D) shows data separation (trial) based on the HR from pupillary response, (E) shows grand average signal in all trial and divided into first and second period from PSV, and (F) shows alpha powers of first and second period using by FFT analysis from pupillary response. In FIG. 9, (G) shows a heart rate (HR) signal from ECG signal, (H) shows EEG signal, (I) shows Data separation (trial) based on HR from ECG signal, (J) shows a grand average signal in all trial and divided into first and second period from the EEG signal, and (K) shows alpha powers of first and second period using by FFT analysis from the EEG signal.

Figure 10A:
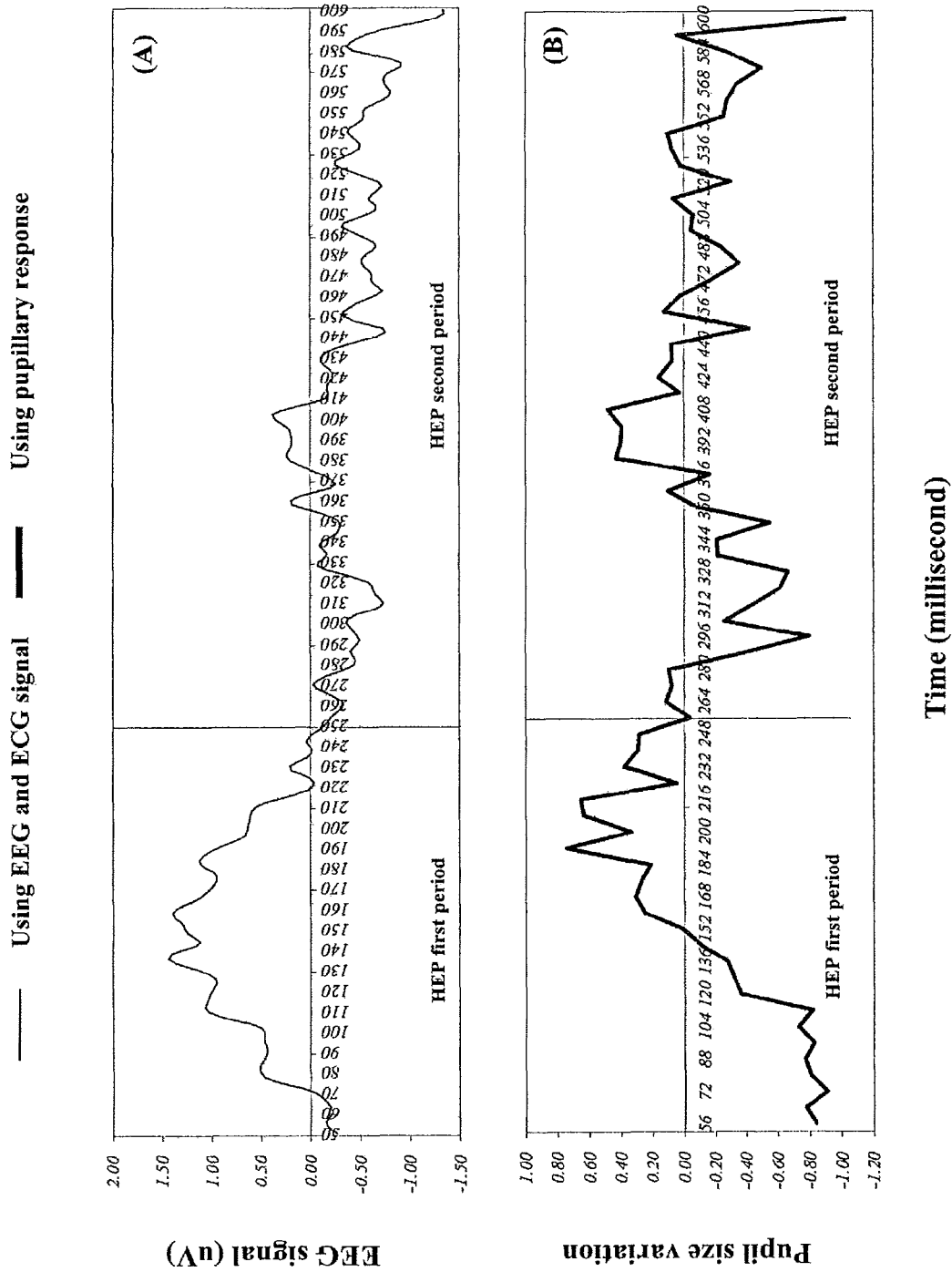
FIGS. 10a and 10b show comparison examples of first and second HEP indexes in a movelessness condition (MNC), according to one or more embodiments.
Figure 10B:
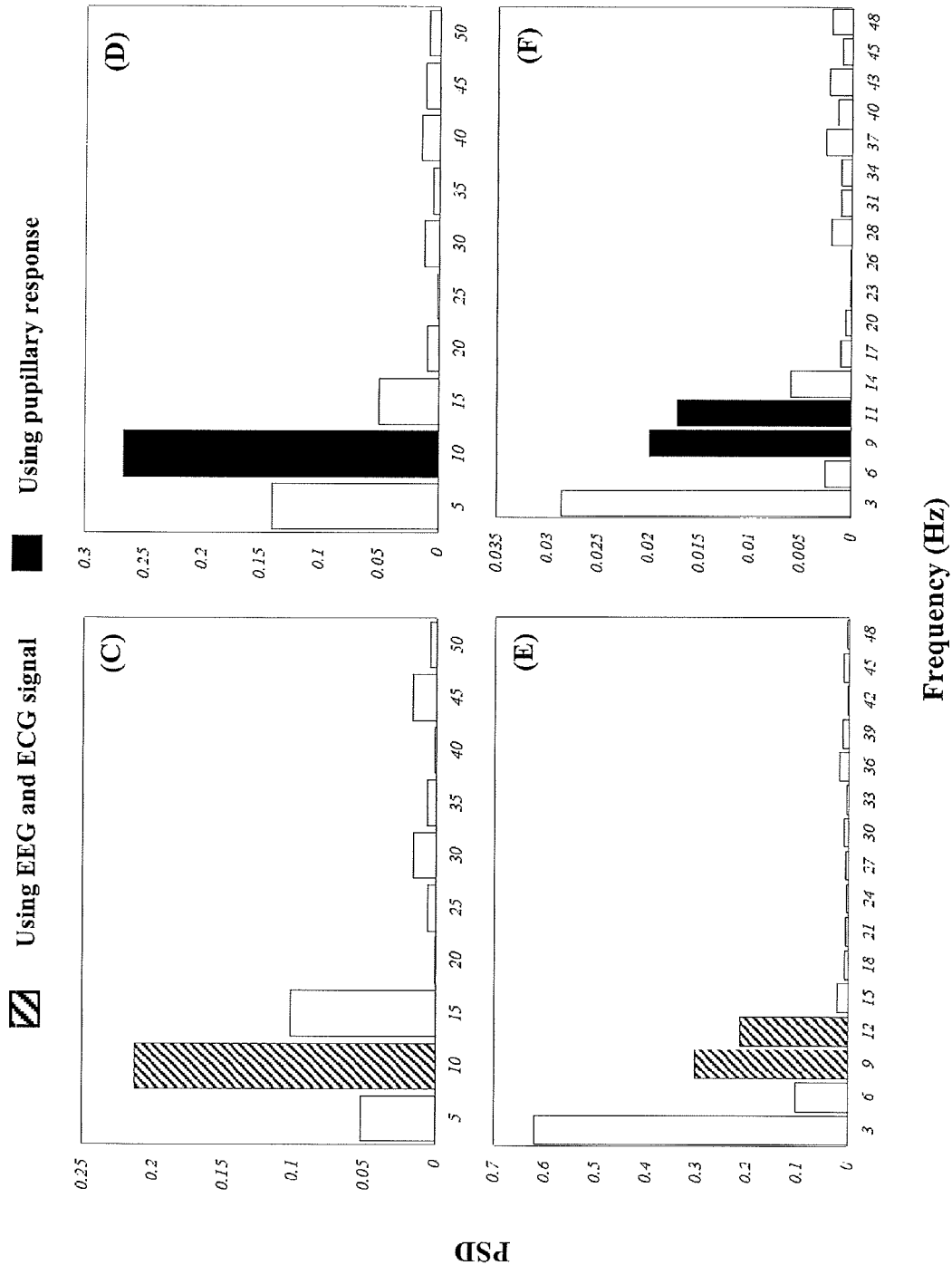

FIGS. 10a and 10b show comparison examples of the first and second index of the HEP in MNC, where A and B: Grand average signal from EEG and PSV, C and D: The alpha powers of first period from EEG (50.276%) and pupil (51.293%), E and F: the alpha power of second period from EEG (37.673%) and pupil (36.636%).

Figure 11:
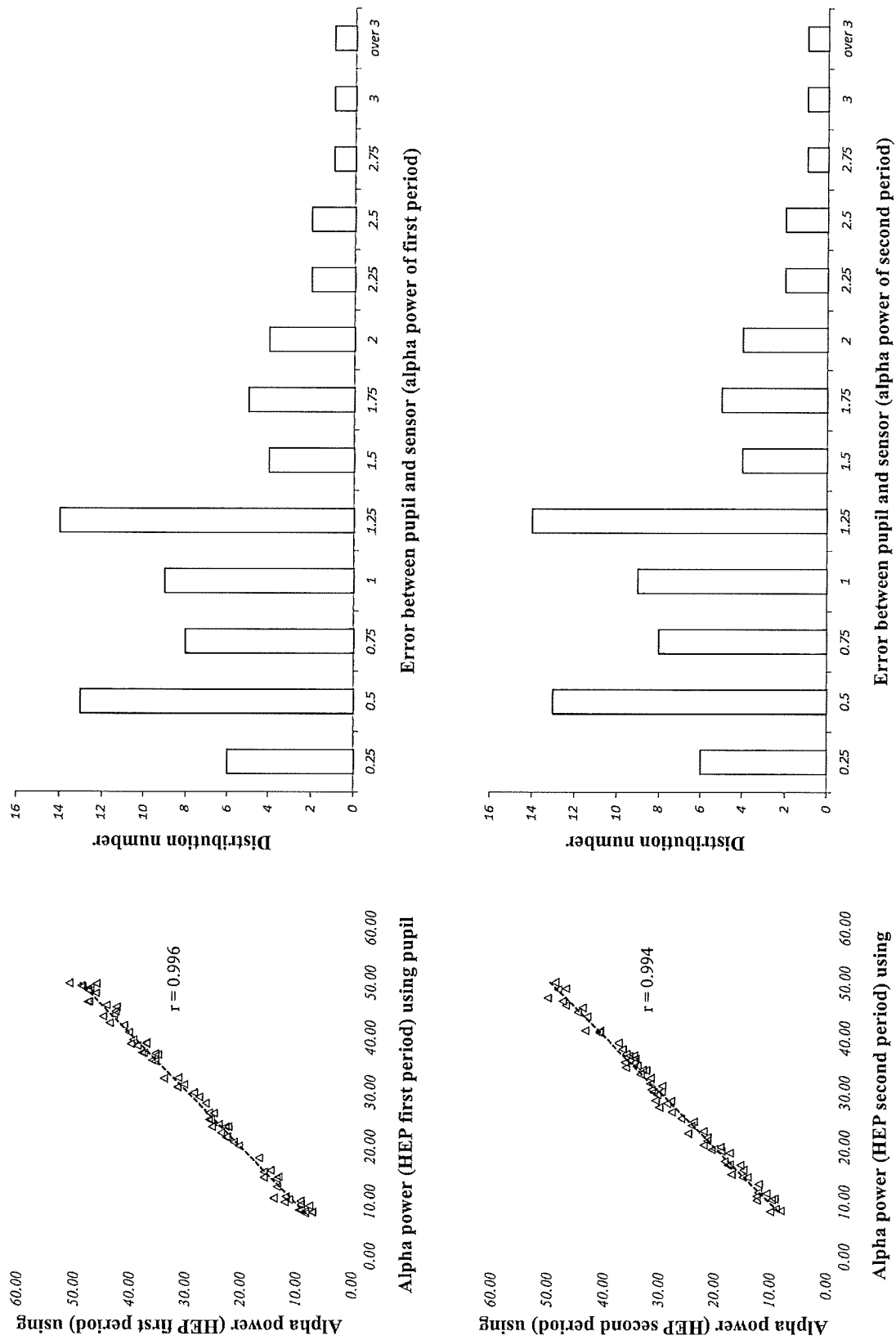
FIG. 11 shows comparison results for correlation and error in the first and second HEP indexes (MNC) for the ground truth, according to one or more embodiments.

FIG. 11 shows comparison results for correlation and error in the first and second indexes of the HEP (MNC) for the ground truth. Referring FIG. 1, the alpha power of the HEP index from the pupillary response indicated a strong correlation for all parameters with r=0.996 for the first period and r=0.994 for the second period. The difference between the mean error of all the parameters was low with ME=1.071 (in range of 0.100 to 3.600) for the first period and ME=1.048 (in range of 0.060 to 3.090) for the second period. The error of the alpha power in the first period was distributed as follows: 1 (35), 1.25 to 3 (33), and over 3 (2). The error of alpha power in the second period was distributed as follows: 1 (36), 1.25 to 3 (33), and over 3 (1). This procedure used recorded data for 300 s. The correlation and mean error were the mean value for the 70 test subjects (N=70), as shown in Table 4.

TABLE 4

| | Alpha power of first period | | | Alpha power of second period | | |
|---|---|---|---|---|---|---|
| Subjects | Using pupil | Using sensor | Error (diff) | Using pupil | Using sensor | Error (diff) |
| S1 | 8.16 | 9.37 | 1.210 | 27.71 | 28.48 | 0.770 |
| S2 | 36.63 | 35.37 | 1.260 | 36.46 | 34.35 | 2.110 |
| S3 | 10.52 | 11.70 | 1.180 | 31.31 | 31.50 | 0.190 |
| S4 | 49.51 | 50.82 | 1.310 | 29.82 | 29.50 | 0.320 |

TABLE 4-continued

| | Alpha power of first period | | | Alpha power of second period | | |
|---|---|---|---|---|---|---|
| Subjects | Using pupil | Using sensor | Error (diff) | Using pupil | Using sensor | Error (diff) |
| S5 | 48.94 | 48.47 | 0.470 | 14.25 | 14.74 | 0.490 |
| S6 | 9.80 | 9.10 | 0.700 | 16.46 | 17.09 | 0.630 |
| S7 | 49.11 | 48.69 | 0.420 | 12.92 | 11.89 | 1.030 |
| S8 | 42.26 | 43.56 | 1.300 | 17.11 | 18.01 | 0.900 |
| S9 | 43.45 | 44.71 | 1.260 | 29.79 | 30.94 | 1.150 |
| S10 | 30.62 | 31.30 | 0.680 | 29.25 | 30.25 | 1.000 |
| S11 | 23.26 | 25.13 | 1.870 | 10.06 | 12.17 | 2.110 |
| S12 | 15.15 | 15.71 | 0.560 | 46.89 | 49.98 | 3.090 |
| S13 | 38.49 | 39.74 | 1.250 | 11.43 | 11.92 | 0.490 |
| S14 | 41.87 | 41.01 | 0.860 | 32.32 | 31.37 | 0.950 |
| S15 | 38.66 | 37.07 | 1.590 | 36.78 | 35.77 | 1.010 |
| S16 | 36.85 | 37.42 | 0.570 | 24.32 | 23.75 | 0.570 |
| S17 | 38.48 | 37.07 | 1.410 | 19.23 | 20.36 | 1.130 |
| S18 | 8.14 | 8.98 | 0.840 | 38.73 | 37.21 | 1.520 |
| S19 | 13.80 | 13.38 | 0.420 | 18.63 | 17.08 | 1.550 |
| S20 | 8.89 | 7.57 | 1.320 | 23.63 | 24.06 | 0.430 |
| S21 | 28.72 | 27.50 | 1.220 | 16.44 | 17.46 | 1.020 |
| S22 | 21.46 | 22.31 | 0.850 | 40.93 | 43.26 | 2.330 |
| S23 | 35.46 | 35.94 | 0.480 | 40.55 | 40.78 | 0.230 |
| S24 | 27.57 | 26.31 | 1.260 | 33.80 | 32.80 | 1.000 |
| S25 | 24.63 | 25.31 | 0.680 | 46.32 | 47.27 | 0.950 |
| S26 | 38.13 | 38.62 | 0.490 | 43.54 | 42.89 | 0.650 |
| S27 | 36.52 | 34.86 | 1.660 | 20.89 | 21.21 | 0.320 |
| S28 | 25.86 | 25.71 | 0.150 | 34.26 | 35.90 | 1.640 |
| S29 | 35.30 | 35.41 | 0.110 | 30.89 | 29.41 | 1.480 |
| S30 | 30.55 | 31.37 | 0.820 | 44.36 | 44.58 | 0.220 |
| S31 | 15.34 | 14.46 | 0.880 | 22.18 | 24.70 | 2.520 |
| S32 | 24.62 | 25.72 | 1.100 | 35.17 | 36.08 | 0.910 |
| S33 | 48.33 | 47.55 | 0.780 | 28.09 | 27.75 | 0.340 |
| S34 | 21.36 | 22.51 | 1.150 | 35.85 | 34.18 | 1.670 |
| S35 | 10.01 | 11.14 | 1.130 | 33.01 | 33.25 | 0.240 |
| S36 | 23.29 | 22.59 | 0.700 | 28.22 | 30.61 | 2.390 |
| S37 | 45.43 | 44.18 | 1.250 | 49.78 | 48.60 | 1.180 |

Figure 12A:
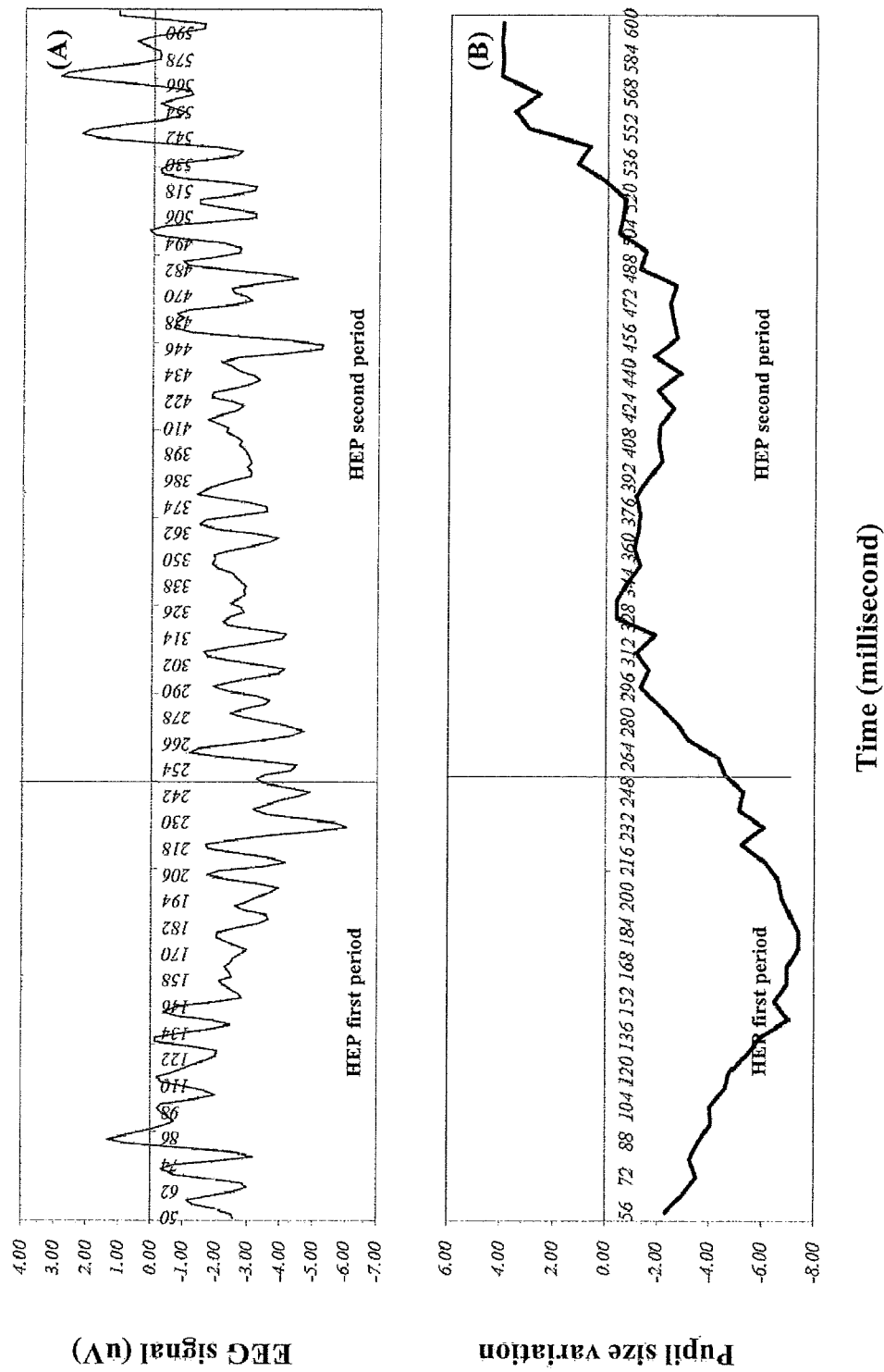
FIGS. 12a and 12b show examples of extracting the HEP index from a pupillary response signal (PSV) and sensor signals (EEG) of test subjects, according to one or more embodiments.
Figure 12B:
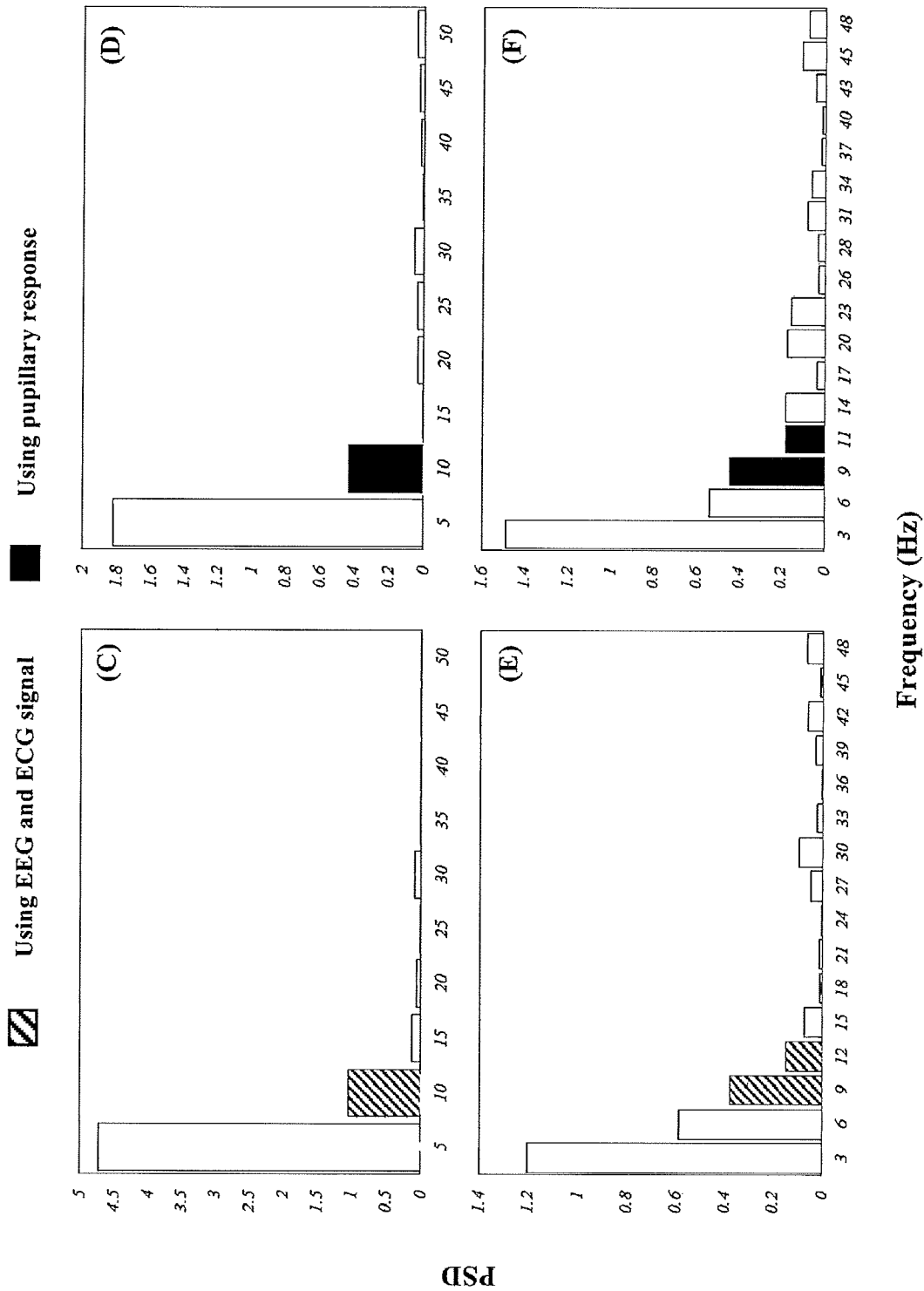

FIGS. 12a and 12b show examples of extracting the HEP indexes from the pupillary response signal (PSV) and sensor signals (EEG) in the test subjects.

In FIG. 12a, (A) and (B) show grand average signal from the EEG and PSV respectively. In FIG. 12b, (C) and (D) show alpha power (15.665%, 17.143%) of HEP first period from EEG and PSV respectively, and (E) and (F) show alpha power (14.886%, 16.505%) of HEP second period from EEG and PSV respectively.

Figure 13:
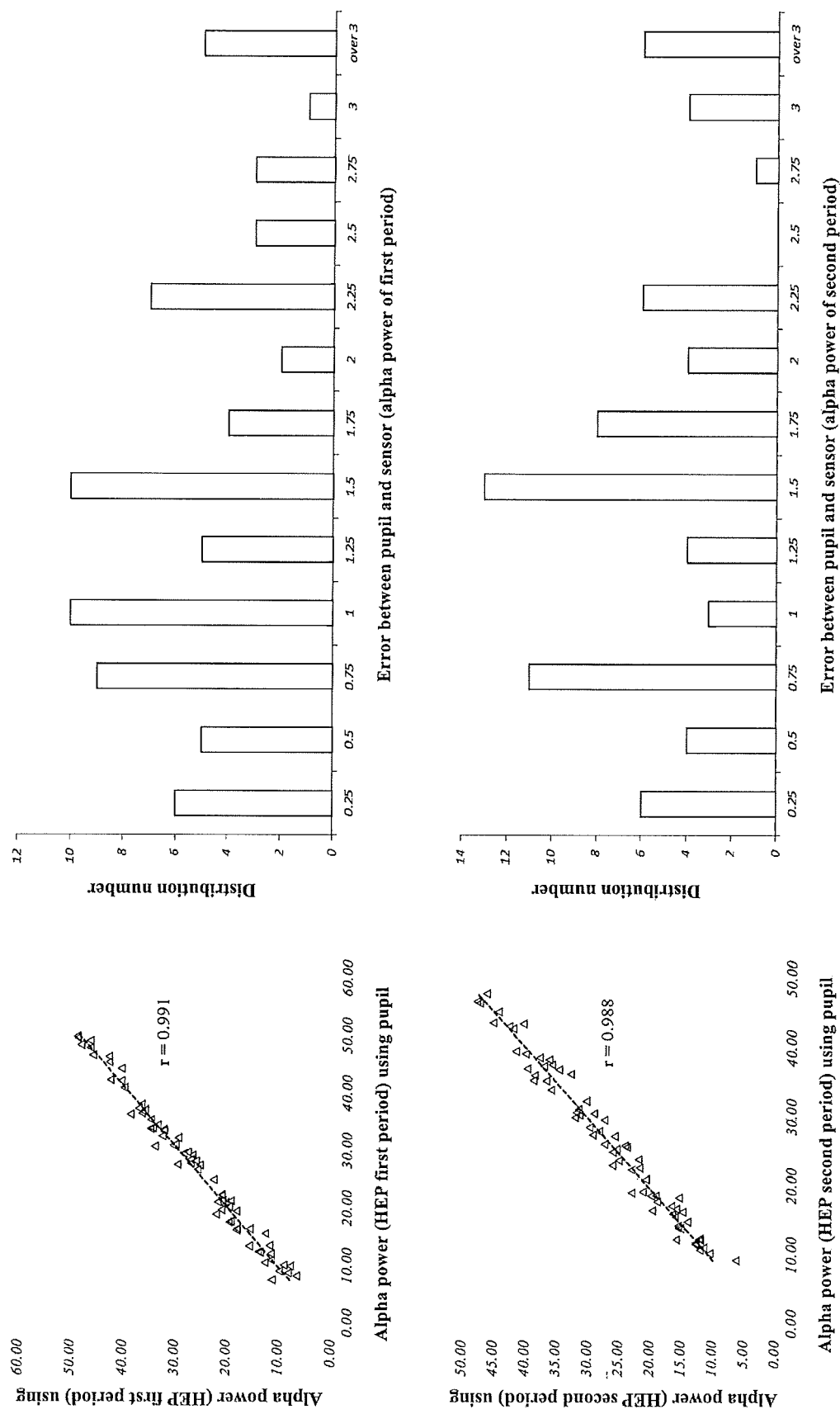
FIG. 13 shows a comparison of the results for the ground truth in the MNC, according to one or more embodiments.

FIG. 13 shows a comparison of the results for the ground truth in MNC. Referring FIG. 13, the alpha power of the HEP index from the pupillary response indicated a strong correlation for all parameters with r=0.991 for first period and r=0.988 for the second period. The difference between the mean error of all parameters was low with ME=1.415 (in range of 0.010 to 3.900) for first period and ME=1.489 (in range of 0.040 to 4.160) for the second period. The error of the alpha power in the first period was distributed as follows: 1 (30), 1.25 to 3 (35), and over 3 (5). The error of the alpha power in the second period was distributed as follows: 1 (24), 1.25 to 3 (40), and over 3 (6). This procedure used recorded data for 300 s. The correlation and mean error were the mean value for the 70 test subjects (N=70), as shown in Table 5.

Table 5 shows averages of mean error in alpha power of first and second periods of the HEP in NMC (N=70)

TABLE 5

| Subjects | Alpha power of first period | | | Alpha power of second period | | |
|---|---|---|---|---|---|---|
| | Using pupil | Using sensor | Error (diff) | Using pupil | Using sensor | Error (diff) |
| S1 | 12.10 | 13.59 | 1.490 | 43.25 | 44.96 | 1.710 |
| S2 | 8.35 | 7.96 | 0.390 | 11.18 | 12.59 | 1.410 |
| S3 | 19.83 | 19.27 | 0.560 | 42.40 | 41.79 | 0.610 |
| S4 | 24.58 | 22.40 | 2.180 | 34.90 | 38.62 | 3.720 |
| S5 | 33.16 | 31.88 | 1.280 | 38.27 | 37.53 | 0.740 |
| S6 | 17.14 | 19.35 | 2.210 | 34.89 | 36.53 | 1.640 |
| S7 | 20.67 | 21.51 | 0.840 | 27.13 | 29.07 | 1.940 |
| S8 | 20.89 | 18.89 | 2.000 | 25.71 | 27.20 | 1.490 |
| S9 | 13.14 | 11.47 | 1.670 | 15.18 | 15.81 | 0.630 |
| S10 | 17.27 | 18.88 | 1.610 | 13.55 | 14.91 | 1.360 |
| S11 | 45.98 | 42.61 | 3.370 | 28.17 | 29.61 | 1.440 |
| S12 | 9.57 | 7.55 | 2.020 | 30.80 | 31.35 | 0.550 |
| S13 | 31.85 | 29.13 | 2.720 | 12.05 | 11.88 | 0.170 |
| S14 | 29.32 | 27.37 | 1.950 | 42.73 | 42.36 | 0.370 |
| S15 | 16.00 | 15.26 | 0.740 | 18.83 | 20.98 | 2.150 |
| S16 | 43.94 | 40.18 | 3.760 | 11.87 | 15.61 | 3.740 |
| S17 | 37.61 | 36.29 | 1.320 | 16.13 | 19.50 | 3.370 |
| S18 | 20.60 | 19.88 | 0.720 | 22.00 | 22.87 | 0.870 |
| S19 | 27.32 | 26.74 | 0.580 | 43.15 | 40.21 | 2.940 |
| S20 | 20.99 | 20.57 | 0.420 | 47.52 | 46.00 | 1.520 |
| S21 | 28.78 | 26.44 | 2.340 | 37.96 | 36.01 | 1.950 |
| S22 | 30.68 | 29.67 | 1.010 | 15.87 | 14.67 | 1.200 |
| S23 | 26.35 | 25.41 | 0.940 | 16.76 | 16.43 | 0.330 |
| S24 | 15.83 | 17.84 | 2.010 | 13.85 | 15.37 | 1.520 |
| S25 | 41.78 | 40.19 | 1.590 | 30.35 | 31.66 | 1.310 |
| S26 | 33.30 | 32.00 | 1.300 | 46.37 | 47.47 | 1.100 |
| S27 | 16.06 | 17.65 | 1.590 | 29.25 | 27.18 | 2.070 |
| S28 | 36.10 | 36.17 | 0.070 | 24.99 | 25.24 | 0.250 |
| S29 | 10.18 | 12.39 | 2.210 | 33.58 | 35.71 | 2.130 |
| S30 | 32.20 | 32.21 | 0.010 | 9.96 | 10.33 | 0.370 |
| S31 | 30.35 | 33.66 | 3.310 | 15.64 | 16.24 | 0.600 |
| S32 | 33.48 | 34.48 | 1.000 | 25.31 | 23.59 | 1.720 |
| S33 | 36.01 | 38.43 | 2.420 | 36.48 | 34.47 | 2.010 |
| S34 | 19.37 | 20.77 | 1.400 | 29.63 | 31.87 | 2.240 |
| S35 | 46.24 | 45.66 | 0.580 | 25.54 | 23.93 | 1.610 |
| S36 | 33.55 | 34.04 | 0.490 | 46.11 | 47.08 | 0.970 |
| S37 | 40.56 | 39.58 | 0.980 | 38.84 | 39.82 | 0.980 |
| S38 | 7.83 | 6.44 | 1.390 | 11.29 | 12.54 | 1.250 |
| S39 | 48.05 | 47.87 | 0.180 | 18.29 | 19.69 | 1.400 |
| S40 | 7.14 | 11.04 | 3.900 | 23.36 | 24.86 | 1.500 |
| S41 | 47.50 | 46.13 | 1.370 | 27.57 | 28.07 | 0.500 |
| S42 | 19.10 | 17.81 | 1.290 | 36.69 | 39.59 | 2.900 |
| S43 | 37.01 | 36.84 | 0.170 | 11.79 | 11.83 | 0.040 |
| S44 | 36.52 | 35.96 | 0.560 | 18.70 | 22.86 | 4.160 |
| S45 | 34.09 | 33.10 | 0.990 | 37.04 | 36.84 | 0.200 |
| S46 | 44.99 | 42.47 | 2.520 | 26.88 | 25.52 | 1.360 |
| S47 | 41.89 | 42.22 | 0.330 | 17.99 | 15.19 | 2.800 |
| S48 | 8.72 | 9.60 | 0.880 | 22.64 | 25.93 | 3.290 |
| S49 | 29.16 | 28.08 | 1.080 | 35.65 | 38.37 | 2.720 |
| S50 | 27.10 | 25.02 | 2.080 | 20.60 | 20.53 | 0.070 |
| S51 | 18.58 | 21.92 | 3.340 | 10.46 | 11.90 | 1.440 |
| S52 | 28.07 | 26.78 | 1.290 | 13.61 | 15.33 | 1.720 |
| S53 | 27.80 | 25.80 | 2.000 | 37.26 | 35.55 | 1.710 |
| S54 | 13.02 | 15.33 | 2.310 | 14.47 | 13.91 | 0.560 |
| S55 | 49.28 | 48.48 | 0.800 | 10.69 | 11.27 | 0.580 |
| S56 | 11.76 | 11.24 | 0.520 | 39.16 | 41.38 | 2.220 |
| S57 | 12.04 | 13.25 | 1.210 | 11.91 | 12.06 | 0.150 |
| S58 | 48.74 | 46.10 | 2.640 | 23.48 | 21.68 | 1.800 |
| S59 | 22.02 | 20.75 | 1.270 | 22.27 | 21.56 | 0.710 |
| S60 | 21.81 | 20.73 | 1.080 | 30.17 | 28.89 | 1.280 |
| S61 | 9.76 | 8.80 | 0.960 | 16.32 | 15.59 | 0.730 |
| S62 | 35.02 | 34.40 | 0.620 | 44.86 | 44.12 | 0.740 |
| S63 | 29.07 | 28.11 | 0.960 | 18.23 | 18.93 | 0.700 |
| S64 | 15.18 | 12.28 | 2.900 | 17.43 | 18.69 | 1.260 |
| S65 | 20.18 | 20.12 | 0.060 | 35.85 | 32.62 | 3.230 |
| S66 | 30.56 | 30.13 | 0.430 | 24.57 | 25.83 | 1.260 |
| S67 | 10.63 | 11.16 | 0.530 | 31.90 | 30.08 | 1.820 |
| S68 | 27.16 | 29.30 | 2.140 | 29.95 | 31.18 | 1.230 |
| S69 | 49.50 | 48.53 | 0.970 | 8.96 | 6.13 | 2.830 |
| S70 | 36.73 | 35.56 | 1.170 | 11.34 | 12.66 | 1.320 |
| | | Mean error | 1.415 | | Mean error | 1.489 |

Real-Time System for Detecting the Cardiac Time Domain Parameters

The real-time system for detecting human vital signs was developed using the pupil image from an infrared webcam. This system includes an infrared webcam, near IR (InfraRed light) illuminator (IR lamp) and personal computer for analysis.

The infrared webcam was divided into two types, the fixed type, which is a common USB webcam, and the portable type, which are represented by wearable devices. The webcam was a HD Pro C920 from Logitech Inc. converted into an infrared webcam to detect the pupil area.

Figure 14:
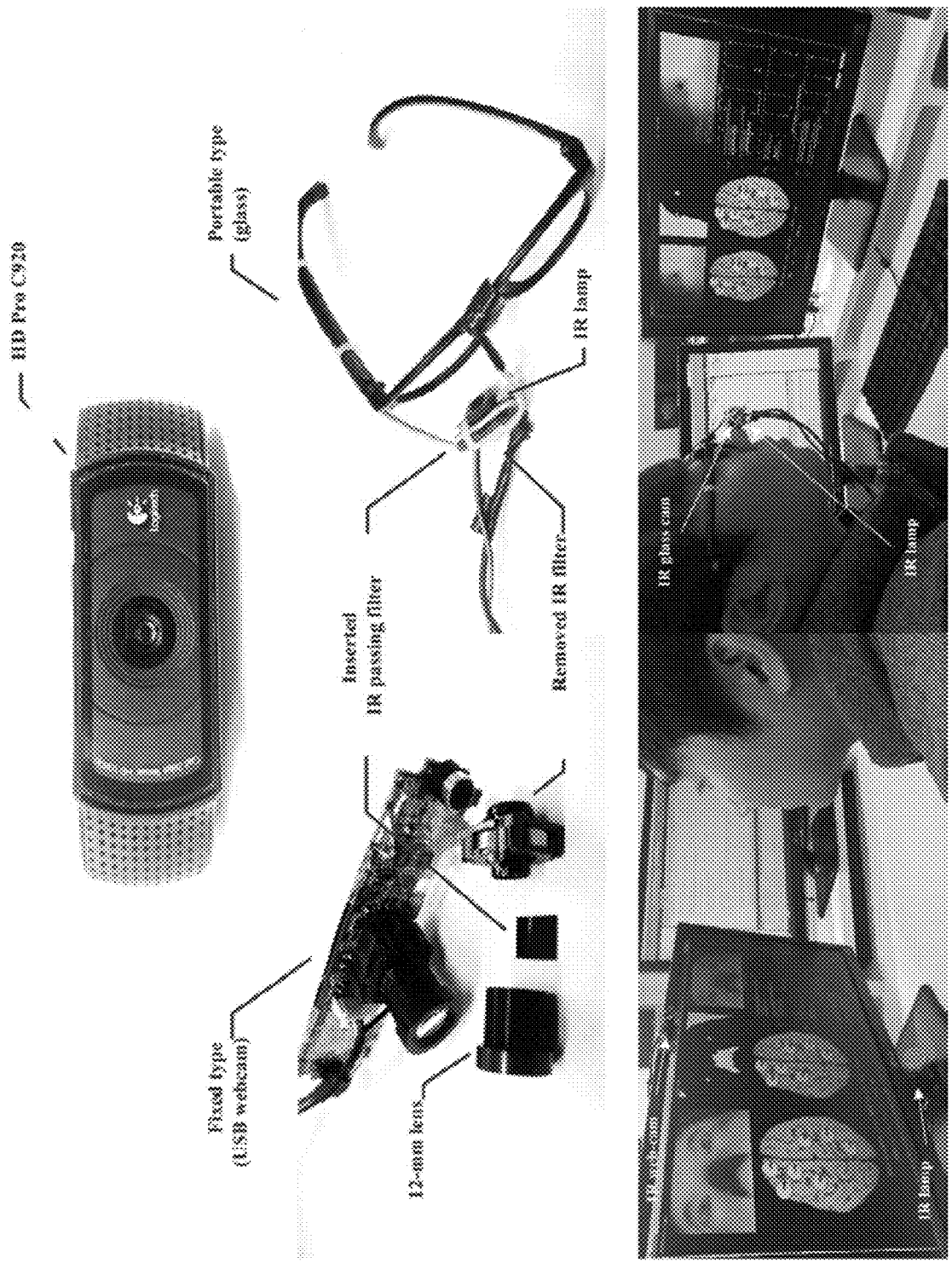
FIG. 14 shows an infrared webcam system for capturing pupil images, according to one or more embodiments.

The IR filter inside the webcam was removed and an IR passing filter used for cutting visible light from Kodac Inc., was inserted into the webcam to allow passage of IR wavelength longer than 750 nm, as shown in FIG. 14. The 12-mm lens inside the webcam was replaced with a 3.6-mm lens to allow for focusing on the image when measuring the distance from 0.5 m to 1.5 m.

FIG. 14 shows an infrared webcam system for taking pupil images.

The conventional 12 mm lens of the USB webcam shown in FIG. 12 was replaced with a 3.6 mm lens so that the subject could be focused when a distance of 0.5 m to 1.5 m was photographed.

Figure 15:
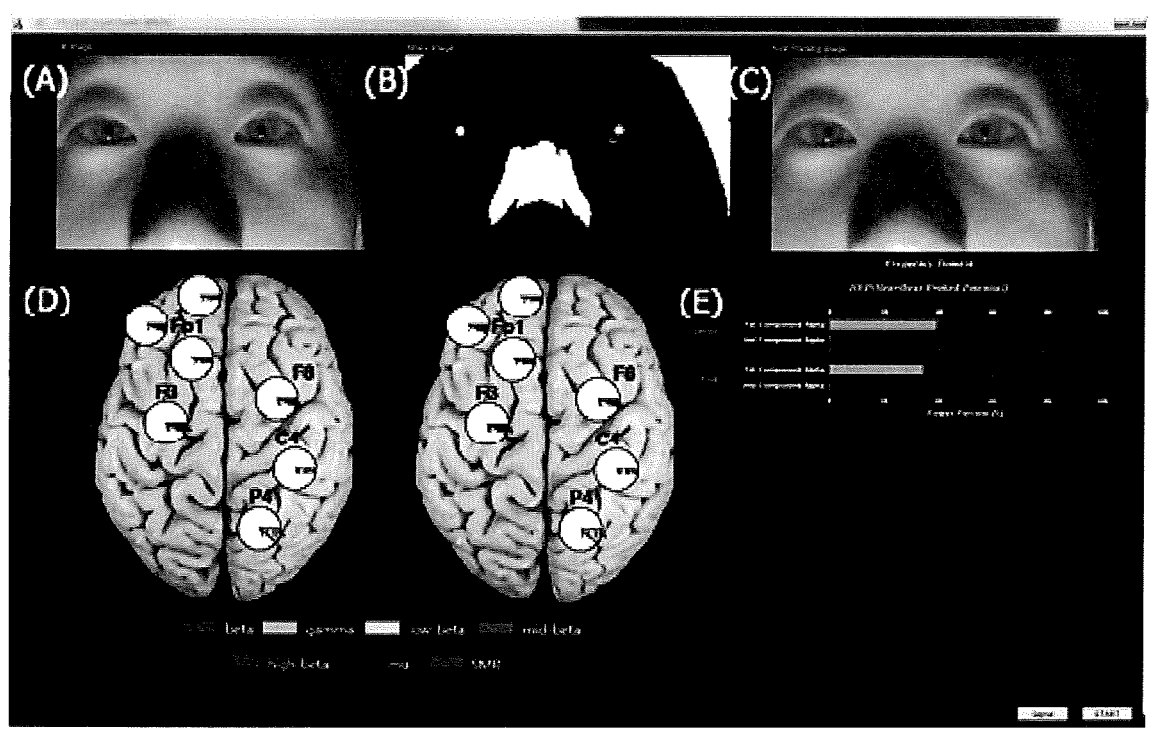
FIG. 15 shows an interface screen of a real-time system, according to one or more embodiments.

FIG. 15 shows an interface screen of a real-time system for detecting and analyzing a biological signal from an infrared webcam and a sensor, where (A): Infrared pupil image (input image), (B): binarized pupil image, (C): Detecting the pupil area, (D): Output of cardiac time parameters, (E): Output of cardiac frequency parameters (VLF power, LF power, HF power, VLF/HF ratio, and LF/HF ratio). (F): Output of EEG spectral parameters (low beta power in FP1, mid beta power in FP1, SMR power in FP1, beta power in F3, high beta power in F8, mu power in C4, and gamma power in P4), and (G): Output of HEP parameters (alpha power of HEP first and second components).

As described in the above, the present invention develops and provides an advanced method for measurements of human vital signs from moving images of the pupil. Thereby, the measurement of parameters in cardiac time domain can be performed by using a low-cost infrared webcam system that monitored pupillary response (rhythm). The HEP index represents the alpha power of the first and second components of the HEP.

This result was verified for both the conditions of noise (MNC and NMC) and various physiological states (variation of arousal and valence level by emotional stimuli of sound) for seventy subjects.

The research for this invention examined the variation in human physiological conditions caused by the stimuli of arousal, relaxation, positive, negative, and neutral moods during verification experiments. The method based on pupillary response according to the present invention is an advanced technique for vital sign monitoring that can measure vital signs in either static or dynamic situations.

The proposed method according to the present invention is capable of measuring parameters in cardiac time domain with a simple, low-cost and non-invasive measurement system. The present invention may be applied to various industries such as U-health care, emotional ICT, human factors, HCI, and security that require VSM technology.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of detecting information of brain-heart connectivity, the method comprising:
    obtaining moving images of a pupil and an electrocardiogram (ECG) signal from a subject;
    acquiring a pupil size variation (PSV) from the moving images by separating the moving images based on a predetermined time range after R-peak of the ECG signal;
    extracting signals of a first period and a second period from the PSV and
    calculating alpha powers of the signals of the first and second periods at predetermined frequencies, respectively,
    wherein the first period ranges between 56 ms-348 ms after the R-peak, the second period ranges between 248 ms-600 ms after the R-peak, and each of the alpha powers is obtained from a ratio of a power of the respective frequency thereof to a total power of a total frequency ranging from 0 Hz to 62.5 Hz.

2. The method of claim 1, further comprising repeating the acquiring a predetermined number of times to obtain a plurality of the PSV; and integrating the plurality of the PSV into a PSV based on a grand average technique.

3. The method of claim 1, wherein the frequency of the alpha power of the first period is 10 Hz, and the frequency of the alpha power of the second period is 9 Hz or 11 Hz.

4. A system of detecting information of brain-heart connectivity, the system comprising:
    a video capturing unit configured to capture the moving images of the subject; and
    a computer architecture based analyzing unit, including analysis tools provided by software, configured to perform:
    obtaining moving images of a pupil and an electrocardiogram (ECG) signal from a subject;
    acquiring a pupil size variation (PSV) from the moving images by separating the moving images based on a predetermined time range after R-peak of the ECG signal;
    extracting signals of a first period and a second period from the PSV; and
    calculating alpha powers of the signals of the first and second periods at predetermined frequencies, respectively,
    wherein the first period ranges between 56 ms-348 ms after the R-peak, and the second period ranges between 248 ms-600 ms after the R-peak, and each of the alpha powers is obtained from a ratio of a power of the respective frequency thereof to a total power of a total frequency ranging from 0 Hz to 62.5 Hz.

5. The system of claim 4, wherein the analyzing unit is configured to perform repeating of the acquiring a predetermined number of times to obtain a plurality of the PSV; and integrating the plurality of the PSV into a PSV based on a grand average technique.

6. The system of claim 4, wherein the frequency of the alpha power of the first period is 10 Hz, and the frequency of the alpha power of the second period is 9 Hz or 11 Hz.

* * * * *